United States Patent [19]

Johnson et al.

[11] 4,219,489

[45] Aug. 26, 1980

[54] SYNTHESIS OF STEROIDS

[75] Inventors: William S. Johnson, Portola Valley; Leonard A. Bunes, San Carlos, both of Calif.

[73] Assignee: The Board of Trustees of the Leland Stanford Junior University, Stanford, Calif.

[21] Appl. No.: 939,595

[22] Filed: Sep. 5, 1978

Related U.S. Application Data

[63] Continuation-in-part of Ser. No. 767,727, Feb. 11, 1977, abandoned, which is a continuation of Ser. No. 628,447, Nov. 3, 1975, abandoned, which is a continuation-in-part of Ser. No. 527,830, Nov. 27, 1974, abandoned.

[51] Int. Cl.$^2$ ............................................... C07J 1/00
[52] U.S. Cl. .............................. 260/397.3; 260/397.4; 260/397.5; 260/397.45; 260/327; 568/52; 568/62; 568/715; 568/731; 568/732; 568/308; 568/330; 568/373; 568/371; 568/425; 260/340.9 AS
[58] Field of Search ........................... 260/239.5, 397.5

[56] References Cited

U.S. PATENT DOCUMENTS

| | | | |
|---|---|---|---|
| 3,884,945 | 5/1975 | Johnson et al. | 260/397.45 |
| 4,032,579 | 6/1977 | Johnson | 260/397.45 |

*Primary Examiner*—Elbert L. Roberts
*Attorney, Agent, or Firm*—Bertram I. Rowland

[57] ABSTRACT

Method and compounds are provided for use in the synthesis of steroids wherein a polyolefin is provided having an initiating group having a chalcogen atom in juxtaposition to a double bond, so as to be capable of bond formation to close to form a ring and having a terminating group involving pi unsaturation (a double or triple bond) conjugated to an aromatic ring. Upon acid catalysis, sigma bonds are formed through the interaction of a carbocation formed at the carbon atom bonded to the chalcogen atom and the double bond intermediate the initiating group and the terminating group, which close to form rings of a steroid nucleus, the carbocation interacting with the pi unsaturation conjugated with the aromatic group and being captured by a nucleophile present in the acidic reaction medium. The resulting steroid product may then be modified in known ways to produce known steroids.

8 Claims, No Drawings

SYNTHESIS OF STEROIDS

The invention described herein was made in the course of work under grants or awards from the Department of Health, Education and Welfare and the National Science Foundation.

CROSS REFERENCE TO RELATED APPLICATIONS

This application is a continuation-in-part of application Ser. No. 767,727, filed Feb. 11, 1977 now abandoned which was a continuation of Ser. No. 628,447, filed Nov. 3, 1975, now abandoned, which was a continuation-in-part of Ser. No. 527,830, filed Nov. 27, 1974, now abandoned.

BACKGROUND OF THE INVENTION

1. Field of the Invention

Steroids play an important role in life processes being the basic structure for the male and female hormones, corticosteroids and bile acids, as well as the basis for many synthetic reagents, such as synthetic male and female hormones, anti-inflammatory agents, and the like. The naturally occurring steroids which the synthetic steroids normally mimic have a complex polycyclic structure with particular geometry as to the ring fusions, as well as substituents on the ring, and also have a specific stereoisomerism. Any synthesis must therefore recognize the need to provide a product having the required geometry and stereochemistry.

For the most part the industry has relied on the use of naturally occurring plant steroids which were then modified to provide the necessary substituents. Many of the procedures were fairly extensive since the plant steroids did not provide readily available functionalities at desired sites, such as C-11, nor at sites adjacent to C-11 which would allow for introduction of a particular functionality. In addition, the plant steroids were only difficultly modifiable, where hydrocarbon groups, such as angular methyl groups were modified, either by introducing a polar functionality, or by changing the alkyl group.

In developing a complete synthesis from small molecules to a steroid structure there are a number of considerations. Desirably, resolution which allows for subsequent asymmetric induction should be afforded relatively early in the synthesis. Reactions in the course of the synthesis should not adversely affect earlier geometry. Formation of functionalities should afford the desired spatial configuration upon cyclization. Therefore, a synthetic scheme must be considered as a single entity, in that earlier synthetic steps must anticipate subsequent synthetic steps, and subsequent synthetic steps must take into account their effect on functionalities which have been previously introduced.

2. Description of the Prior Art

Cyclization of monocyclic polyunsaturated compounds has been reported in a number of articles as well as patents. U.S. Pat. Nos. 3,558,672 and 3,598,845 report cyclization of different precursors to the perhydrocyclopentanophenanthrene structure. Scientific articles of interest include Johnson, et al., J. Am. Chem. Soc., 90, 2991 (1968); ibid, 92, 741 (1970); and ibid, 93, 4432 (1971).

SUMMARY OF THE INVENTION

Method and compositions are provided for acid catalyzed cyclization to polycyclic compounds having at least two fused rings. The molecule may be divided into three parts: initiator; linking group; and terminator; the terminator having an aromatic ring conjugated to aliphatic unsaturation, i.e. olefinic and acetylenic. Upon contacting the subject compounds with an acid catalyst, either protonic or Lewis, the compound cyclizes to a fused polycyclic structure, having at least one 5-membered ring. The reaction is carried out in the presence of a nucleophilic reagent which captures the carbocation which forms at the alpha-carbon of the terminating group.

DESCRIPTION OF THE SPECIFIC EMBODIMENTS

A method and compositions are provided for preparing fused polycyclic compounds having at least one 5-membered ring substituted by an aliphatic group. More particularly, the subject invention is concerned with preparing steroid derivatives which are perhydrocyclopentanophenanthrene derivatives, including A-nor compounds. A polyunsaturated compound is employed having a terminating aryl ring conjugated to aliphatic unsaturation, either olefinic or acetylenic, which upon treatment with an acid catalyst, either protonic or Lewis acid, cyclizes to a fused polycyclic structure. By having the appropriate geometry of the aliphatic unsaturation, the resulting compound can be provided with the desired ring geometry.

The compounds of this invention may be divided into three parts referred to as: initiator (Z); linking group (Y); and terminator (X). This molecule (Z—Y—X) is reacted with a nucleophile (WH) under acidic conditions to provide the polycyclic structure. The polyunsaturated compounds employed in this invention will normally have from 15 to 45 carbon atoms, more usually from 16 to 42 carbon atoms and when a steroid nucleus is desired, at least 24 carbon atoms, more usually at least about 26 carbon atoms, and not more than about 42 carbon atoms, more usually not more than about 36 carbon atoms. The compounds will have at least one chalcogen atom (oxygen or sulfur) and may have two or more chalcogen atoms, the chalcogen normally being associated with the initiating group.

The initiator has a chalcogen atom in juxtaposition with a double bond, which upon treatment with acid, results in formation of a carbocation which interacts with the double bond to form a sigma bond or pi bond (depending upon whether the initiator is cyclic or acyclic) and leads to formation of a 5-membered ring either by direct or indirect (through additional double bonds) interaction of the positive charge with the aliphatic unsaturation conjugated with the aromatic ring. Depending upon the nature of the unsaturation and the nucleophile which captures the carbocation, an exo double bond or a heteroatom, particularly chalcogen e.g. oxygen, is introduced at the alpha position.

For the most part the compounds which are subjected to cyclization conditions in the subject invention will have the following formula:

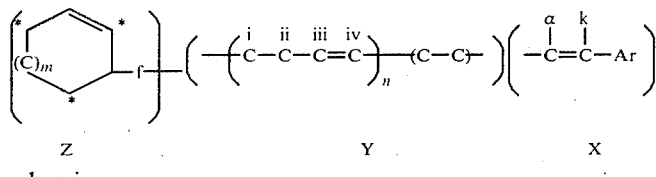

wherein:

the various groups are designated by the letters which have been previously defined as to the portions of the molecule;

for Z:

the * indicate the point of attachment;

f is a substituent bonded to the carbon atom by a chalcogen atom of atomic number 8 to 16 (oxygen or sulfur);

m is 0 or 1, being 1 when the broken line is not a bond;

the broken line indicates the presence of a bond when Z is cyclic and the absence of a bond when Z is acyclic;

for Y:

n is 0, 1 or 2;

the small letter roman numerals indicate the order of the carbon atoms so that 2-iii would be the second 3-butenylene group and the third carbon atom;

the unsatisfied valences of the carbon atoms may be satisfied by hydrogen or alkyl groups, particularly hydrogen and the 2-iii carbon atom will have hydrogen or lower alkyl of from 1 to 3 carbon atoms, more usually of from 1 to 2 carbon atoms, and preferably methyl, the other alkyl groups being of from 1 to 4 carbon atoms, more usually of from 1 to 2 carbon atoms, and preferably methyl, there being not more than 3 alkyl substituents, more usually not more than 2 alkyl substituents, and usually 1 to 2 alkyl substituents; in addition when n is 2 the 2-i carbon atom may be substituted with alkyl as defined above or oxy, including hydroxyl; ethers of from 1 to 6 carbon atoms, particularly saturated aliphatic e.g. methyl and carboxy esters of from 1 to 6, usually 1 to 2 carbon atoms;

for X:

j and k are hydrogen or are taken together to form a pi bond; and

Ar intends a carbocyclic aromatic group of from 6 to 16, usually 6 to 14, preferably 6 to 12 carbon atoms, the aromatic group having from 1 to 2 rings, ether fused or non-fused, e.g. phenyl, biphenyl and naphthyl and having from 0 to 2 chalcogen atoms (O or S) as substituents. By aromatic it is intended that the ring have a total of 6 p and π electrons and is defined as the ability to sustain an induced ring current as determined by nuclear magnetic resonance spectrum. See March, Advanced Organic Chemistry, McGraw Hill Book Co., New York, 1968, pp. 38.

The aromatic ring may be substituted or unsubstituted, generally having from 0 to 2 substituents and from 1 to 2 rings, the substituent having a negative Hammett sigma value, preferably less than about −0.05. The hetero-substituent is normally bonded to an annular ring through a chalcogen atom. The substituents will normally be in other than the ortho position, but the ring may be ortho substituted and the para sigma value will be applied for the ortho substituent. For the most part, the substituents will be chalcoxy, i.e. hydroxy, hydrocarbyloxy, particularly alkoxy, thiol, and hydrocarbylthio, particularly alkylthio, the chalcoxy being of from 0 to 6 carbon atoms, more usually of from 0 to 3 carbon atoms, acylcarboxychalcoxy, i.e. carboxy esters and carboxy thio esters, of from 1 to 6 carbon atoms, more usually of from 2 to 4 carbon atoms, and alkyl of from 1 to 4 carbon atoms, more usually of from 1 to 2 carbon atoms.

(By "hydrocarbyl" is intended a group composed solely of hydrogen and carbon which may be aliphatic, alicyclic, aromatic or combinations thereof and may be aliphatically saturated or unsaturated, usually saturated. In this invention there will usually be not more than one site of ethylenic unsaturation.)

The initiator group Z will normally be of from 5 to 12 carbon atoms, more usually of from 6 to 10 carbon atoms and having from 1 to 4, more usually from 1 to 2 chalcogen atoms, and having from 1 to 2, more usually 1 site of olefinic unsaturation.

The linking group will generally be from 2 to 13 carbon atoms, usually of from 2 to 12 carbon atoms, and more usually of from 2 to 11 carbon atoms, any alkyl substituents most usually being at 2-i and 2-iii, the alkyl group generally being of from 1 to 3 carbon atoms, usually of from 1 to 2 carbon atoms, and preferably methyl, and any oxy, halo, alkenyl or haloalkenyl substituent at 2-i, so that Y forms a chain which is ethylene, 3-hexenylene, or 3,7-decadienylene.

The terminator X is an aryl substituted ethene or ethine having from 6 to 16 carbon atoms, more usually of from 8 to 14 carbon atoms and from 0 to 4 heteroatoms, usually from 0 to 2 heteroatoms, with the ring being substituted or unsubstituted, generally having from 1 to 2 substituents.

I. Intermediates

The cyclization precursor will normally have at least two sites of aliphatic unsaturation, being a diene or enine, but for steroid formation will be a tetraene or trienine. Depending upon whether a bicyclic, tricyclic or tetracyclic compound is formed, the cyclization precursors will have for the most part one of the following formulas:

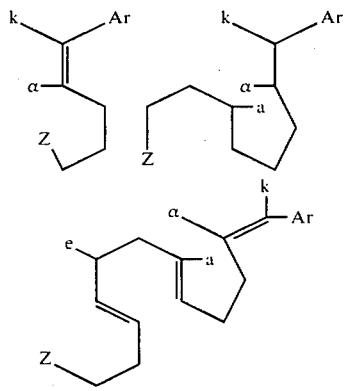

wherein: all of the symbols have been defined previously, except for a and e, and a and e are hydrogen or alkyl of from 1 to 4 carbon atoms, more usually of from 1 to 2 carbon atoms, and more usually methyl, a being preferably hydrogen or methyl, e being preferably hydrogen or methyl, particularly hydrogen, with the proviso that e may also be halo, β-alkenyl or halo-β-alkenyl of 3 to 6, usually 3 to 4 carbon atoms, where halo is vinyl and preferably of atomic number 17 to 35, or oxy including hydroxyl, ether of 1 to 6, usually 1 to 2, carbon atoms, particularly saturated aliphatic, and carboxyester of from 1 to 6 usually 1 to 2 carbon atoms, particularly saturated aliphatic.

The Ar group is a carbocyclic mono or bicyclic aromatic, either fused or non-fused, generally of from 6 to 16 carbon atoms, and preferably of from 6 to 12 carbon atoms, having from 0 to 2 more usually 0 to 1 substituents, which are particularly alkyl of from 1 to 4 carbon atoms, more usually of from 1 to 2 carbon atoms, chalcoxy of from 0 to 6 carbon atoms, more usually of from 0 to 4 carbon atoms, and preferably of from 0 to 2 carbon atoms, and acylcarboxy ester of from 1 to 6 carbon atoms, more usually of from 1 to 4 carbon atoms. Illustrative Ar groups include phenyl, tolyl, anisyl, phenetyl, xylyl, t.-butylphenyl, acetoxyphenyl, mercaptophenyl, naphthyl, biphenyl and dimethoxyphenyl.

More particularly, the precursors to the polycyclic compounds will have the following formula:

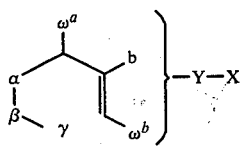

wherein:
the broken line is a bond when the group is cyclic and is not a bond when the group is acyclic;
α is methylene or a bond, being methylene when the broken line is not a bond;
β is alkylidene of from 1 to 8 carbon atoms, usually of from 1 to 6 carbon atoms, more usually of from 1 to 4 carbon atoms having from 0 to 2 alpha-chalcoxy groups, wherein the two chalcoxy groups may be taken together to form a cyclic ketal of from 5 to 6 annular members, and having from 0 to 1 site of ethylenic unsaturation, or with the proviso that the broken line is a bond, of the following formula $\omega^c$—CH=;
γ is alpha-chalcoxyhydrocarbyl having from 1 to 2 alpha-chalcoxy groups and being of from 1 to 10 carbon atoms, more usually of from 1 to 8 carbon atoms and free of aliphatic unsaturation and includes alkyl, cycloalkyl and phenyl substituents on the carbon atom in the chain, and wherein an oxygen atom may bridge to β to form an epoxy group;
when the broken line is a bond, γ is usually alkylidene of from 1 to 6 carbon atoms, more usually of from 1 to 4 carbon atoms and having from 1 to 2 alpha-chalcoxy groups which may be taken together to form a cyclic ketal of from 5 to 6 annular members, and when the broken line is not a bond, γ will be hydrocarbyl having from 1 to 2 alpha-chalcoxy groups which may be taken together to form a cyclic acetal or ketal of from 5 to 6 annular members and is of from 1 to 8 carbon atoms, more usually of from 2 to 8 carbon atoms and free of aliphatic unsaturation, and wherein one of the chalcoxy groups may be taken together with β to form an epoxide ring;
b is hydrogen or lower alkyl of from 1 to 4 carbon atoms, more usually of from 1 to 3 carbon atoms, and preferably of from 1 to 2 carbon atoms and is straight chained; and
one of $\omega^{a-c}$ is a bond to Y and is otherwise hydrogen;
Y has been defined previously, but as the tetracyclic precursor is 5-e-7-a-3,7-decadien-1,10-ylene, where the 1-position is bonded to Z and the 10-position is bonded to X and is of the formula:

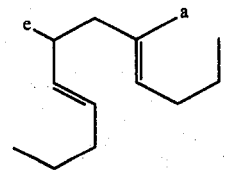

wherein:
a is hydrogen or lower alkyl of from 1 to 4 carbon atoms, usually of from 1 to 3 carbon atoms and preferably of from 1 to 2 carbon atoms, particularly methyl, and usually straight chained;
e is hydrogen, lower alkyl of from 1 to 4 carbon atoms, more usually of from 1 to 2 carbon atoms, preferably methyl, and usually the alpha-configuration; halo, alkenyl or haloalkenyl as previously defined, or oxy including hydroxyl, ether, particularly alkoxy of from 1 to 6, usually 1 to 2 carbon atoms and carboxyester, particularly saturated aliphatic, of from 1 to 6, usually 1 to 2, carbon atoms; and
X has been defined previously.

For the most part the precursors to the tetracyclic steroidal compounds are of primary interest, and for those having a cyclic initiator group, the compound will have the following formula:

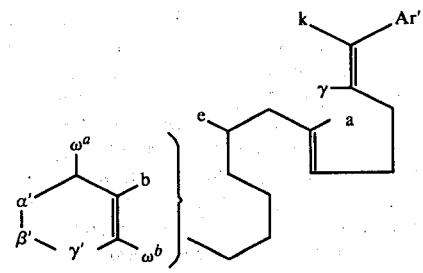

wherein:
a and b are hydrogen or alkyl of from 1 to 4 carbon atoms, more usually of from 1 to 3 carbon atoms, and preferably of from 1 to 2 carbon atoms, particularly methyl with a preferably being alkyl;
α' is a bond or methylene;
β' is alkylidene of from 1 to 8, more usually of from 1 to 6, and preferably of from 1 to 4 carbon atoms, having from 0 to 2 alpha-chalcoxy groups bonded to the annular carbon atom, wherein 2 chalcoxy groups may be taken together to form a cyclic ketal of from 5 to 6 annular members, and having from 0 to 1 site of ethylenic unsaturation, particularly exo unsaturation, that is, a double bond to the annular carbon atom, or of the formula $\omega^c$—CH=;
γ' is alpha-chalcoxyalkylene of from 1 to 8, more usually 1 to 6, and preferably 1 to 4 carbon atoms, having from 1 to 2 chalcoxy groups bonded to the annular carbon atom, wherein two chalcoxy groups may be taken together to form a cyclic ketal of from 5 to 6 annular members;

wherein one of $\omega^{a-c}$ is a bond, but are otherwise hydrogen; and the remaining symbols have all been defined previously.

When Z is acyclic, those compounds used for preparation of the steroid nucleus will for the most part have the following formula:

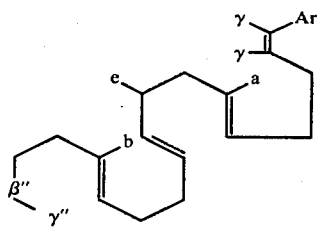

wherein:

$\beta''$ is an aliphatic hydrocarbylidene group having from 0 to 2 alpha-chalcoxy substituents and from 0 to 1 site of ethylenic unsaturation, particularly $\Delta^1$ and is of 1 to 8 carbon atoms, more usually of from 1 to 6 carbon atoms, and preferably of from 1 to 4 carbon atoms, and usually methylene and may be taken together with $\gamma''$ to form an epoxide ring;

$\gamma''$ is chalcoxymethyl of from 1 to 12 carbon atoms, more usually of from 1 to 10 carbon atoms, preferably of from 1 to 8 carbon atoms, and more preferred of from 1 to 5 carbon atoms, having from 1 to 2 alpha-chalcoxy groups where two alpha-chalcoxy groups may be taken together to form a cyclic ketal of from 5 to 6 annular members, and one chalcoxy group may be taken together with $\beta''$ to form an epoxide ring;

$\gamma''$ may be substituted with aliphatically saturated hydrocarbyl groups—alkyl, cycloalkyl, or carbocyclic aryl groups—of from 1 to 8 carbon atoms, more usually of from 1 to 6 carbon atoms, and when other than aryl, of from 1 to 2 carbon atoms, particularly methyl; and the remaining symbols have been defined previously.

II. Methods of Preparing Intermediates

The cyclization precursors or intermediates are conveniently prepared by joining a molecule having the initiator group Z with a molecule having the terminating group X so as to provide intermediate unsaturation which is involved in the cyclization. Conveniently, a Schlosser-Wittig condensation can be employed providing primarily the trans configuration, which provides the desired ring fusion geometry upon cyclization.

The preparation of the various fragments, which contain the Z group for condensation with the aldehyde, has appeared in a number of references and will be further disclosed in the experimental section. The following publications are therefore cited to demonstrate the synthesis of a number of different Z group containing fragments.

Johnson, Accounts of Chem. Research, 1968, 1: Johnson, et al., J. Am. Chem. Soc., 90, 299 (1968); Johnson and Schaaf, Chemical Comm., 1969, 671; Abrams, et al., Bioorganic Chemistry, 1, 243 (1971); Johnson, et al., J. Am. Chem. Soc., 93 4332 (1971); Johnson, et al., ibid, 92, 4461 (1972). U.S. Pat. Nos. 3,558,672 and 3,598,845 and German Offenlegungsschrift Nos. P22 34 018.7 and P24 18 877.0.

The Schlosser-Wittig reaction combines in an ethereal solvent approximately equimolar amounts of the ylide, particularly the triphenylphosphonium ylide, with the appropriate aldehyde. An ethereal solvent is employed, e.g. tetrahydrofuran, diethyl ether, dimethoxyethylene and combinations thereof. The temperature will normally be about $-90°$ to $-50°$ C. and the concentrations of reactants will generally be from about 0.05 to 1 M, usually from about 0.1 to 0.5 M. Carbocyclic aryl lithium, e.g. phenyllithium is added in at least about equimolar amount and usually in excess, ranging from about 1 to 2 moles per mole of ylide-aldehyde reactant. The temperature is allowed to rise to from about $-50°$ to $-10°$ C. and after a sufficient time, e.g. 5 min to 1 hour, the reaction is quenched, e.g. by addition of a lower alkanol, for example, methanol. The product may then be isolated and purified according to conventional procedures.

The course of the reaction generally may be described in the following Chart I,

CHART I

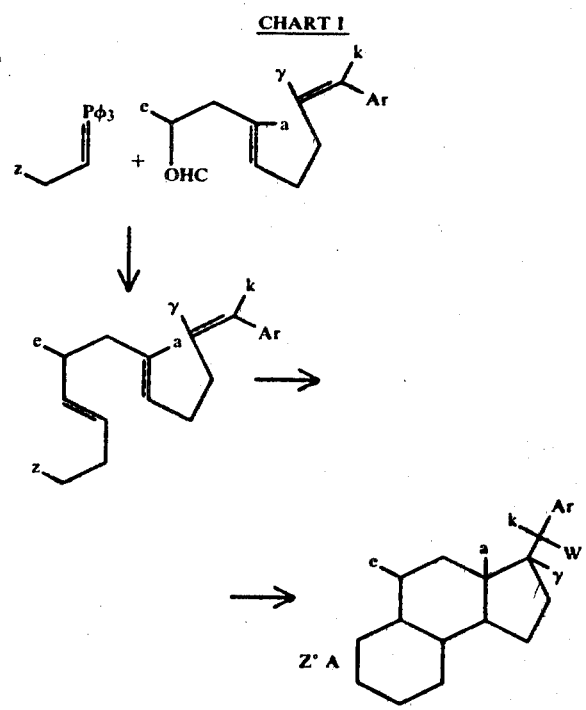

Z* indicates the residue of the A ring of the steroid, varying with Z. The other symbols have been defined previously.

The next chart describes a specific preparation employing a styryl terminating group and showing the various transformations of the intermediates to the cyclization precursor.

CHART II

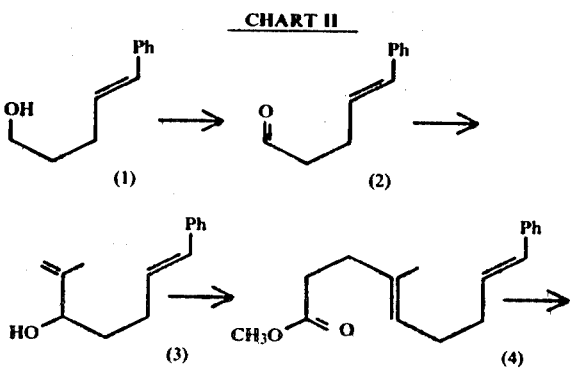

-continued
CHART II
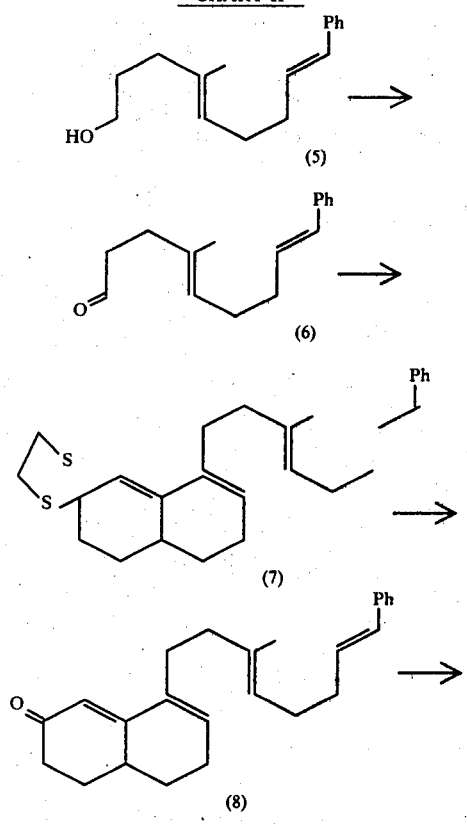
-continued
CHART II
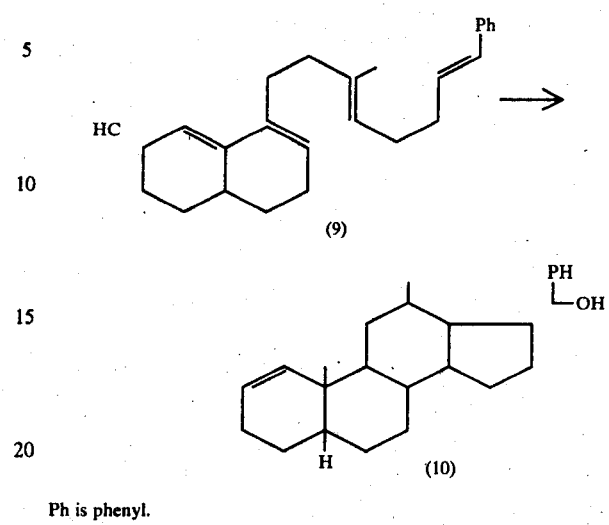
Ph is phenyl.
In the next chart the procedure for preparing the cyclization precursor is described where the terminating group is phenylethinyl.
CHART III
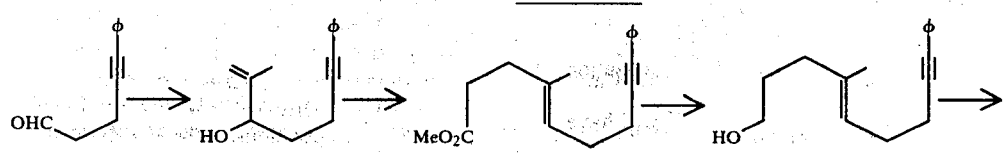

-continued
CHART III

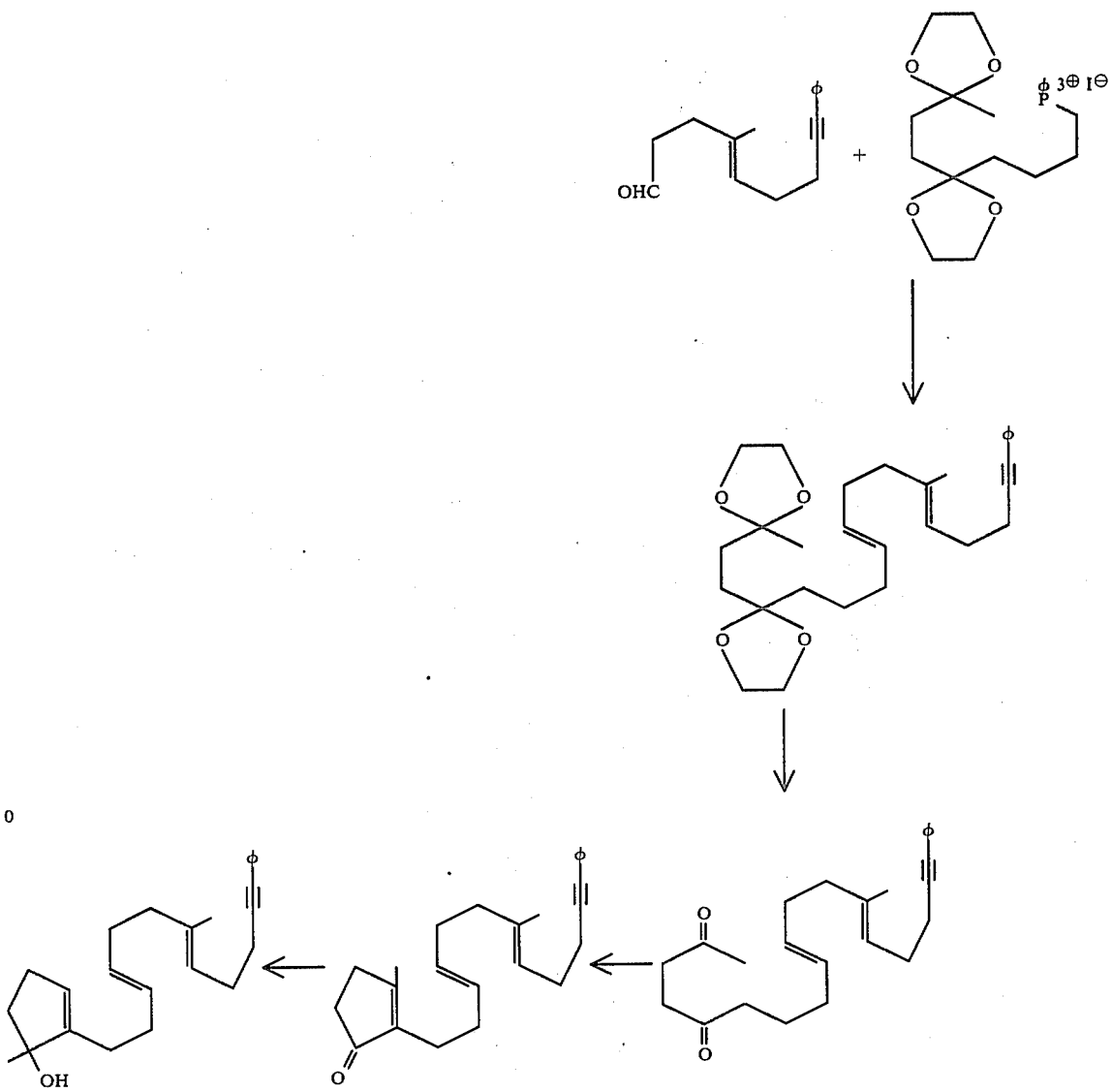

In accordance with the procedures of the subject invention, polyunsaturated compounds are prepared which have the desired geometry, so that on cyclization the steroidal product has the naturally occurring configuration. During the course of the reaction, the double bonds which are introduced are introduced in such a manner as to provide the necessary geometry.

The terminating group plays the role in accepting a positive charge and reacting with a nucleophile before undesirable side reactions may occur, particularly Wagner-Meerwein rearrangements. The pi unsaturation conjugated to the aromatic group affords a benzyl type carbonium ion which is stabilized by conjugation with the aromatic ring. Therefore, groups bonded to the aromatic ring should stabilize positive charges so as to reduce the energy of the system and yet allow for reaction with a nucleophile in preference to a reorganization of the base molecule.

For the most part the terminating group X will have the following formula:

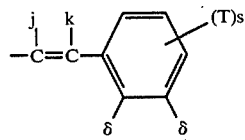

wherein:
j and k are hydrogen or are taken together to form a pi bond;
δ is hydrogen or the two δ's may be taken together to form a 1,3-butadienylene-1,4;
T is alkyl of from 1 to 4 carbon atoms, phenyl, oxy (hydroxy or hydrocarbyloxy, particularly alkoxy, of from 1 to 6 usually 1 to 4 carbon atoms), thio (mercapto or hydrocarbylthio, particularly alkylthio, of from 1 to 6, more usually 1 to 4 carbon atoms), carboxy esters of from 1 to 6 carbon atoms, and the like;
s is 0 to 2, more usually 0 to 1, wherein T can be in the ortho, meta or para positions, usually being in the meta or para positions.

III. Cyclization

The cyclization is carried out in a protic or aprotic solvent in the presence of a Lewis acid (includes protonic) and optionally in the presence of a nucleophile other than supplied by the solvent or Lewis acid. The solvent and nucleophile may be the same or different, and when a solvent is employed in combination with the nucleophile, the solvent will normally be inert and aprotic.

A wide variety of solvents may be employed, which may be used by themselves or in combination with a nucleophilic reagent. Particularly useful solvents are halocarbon, both chloro and fluoro, normally of from 1 to 8 carbon atoms, and varying from monosubstituted to persubstituted and having from 0 to 1 site of ethylenic unsaturation, particularly when polyhalo substituted. Illustrative solvents include methylene chloride, 1,2-dichloroethane, 1,1-dichloroethylene, 1,1-difluoroethane, hexafluorobenzene, perfluoromethylcyclohexane, 1,1,2-trichloro-1,2,2-trifluoroethane, etc. Haloethers may also be employed, such as perfluoro-2-butyltetrahydrofuran, bis-2,2-trifluoroethyl ether, etc. Saturated hydrocarbons may also be employed such as hexane, heptane, cyclohexane, etc.

The nucleophile, which may also serve as the solvent, has a pair of electrons which may coordinate with a carbocation to form a covalent bond, e.g. a Lewis base, particularly a Bronsted base. The nucleophiles, which are employed, are relatively weak nucleophiles and include carbocyclic aromatics, e.g. benzene, toluene, anisole, etc.; olefinic hydrocarbons of from about 4 to 10 carbon atoms, e.g. 1-pentene, 2-pentene, isohexene, 1-heptene, 2-heptene, styrene, etc.; nitroalkanes of from about 1 to 6 carbon atoms having an alpha-hydrogen, e.g. nitromethane, 1-nitropropane, 2-nitropropane, etc.; water; and fluorinated alcohols, e.g. 2,2,2-trifluoroethanol, s-hexafluoroisopropanol, 2,2,3,3-pentafluoropropanol, etc. Peculiar nucleophiles which form a stable carbocation or orthoester are the cyclic esters of carbonic acid, e.g. ethylene carbonate.

The solvents and nucleophiles will normally have the following properties: (1) relatively low boiling point; (2) remain liquid in the reaction mixture at the reaction temperature; (3) provide some solubilization of the reactants; and (4) do not undergo acid catalyzed reactions under the reaction conditions.

A wide variety of acidic catalysts may be used. For the purpose of this invention, Lewis acids shall include both protic and aprotic catalysts. The protonic catalysts are strong acids, preferably carboxylic acids, having a pK 20° C. in an aqueous solution of less than 4, preferably less than about 2. Illustrative strong protonic acids include trifluoroacetic acid, trichloroacetic acid, formic acid, etc. Illustrative aprotic Lewis acids include stannic chloride, titanium tetrachloride, zinc chloride, zinc bromide, boron trifluoride, etc.

The choice of acidic catalysts will affect the course of the reaction in that it may act as a nucleophile as well as a catalyst. The protonic catalyst may compete with nucleophiles present in solution to form vinyl esters, e.g. trifluoroacetate esters, when trifluoroacetic acid is employed. The metal halides, particularly chlorides and bromides, will act to provide halide as a nucleophile. Thus halides will be formed. Where a variety of nucleophiles are present, such as the acid catalyst and an independent nucleophile, a large excess of the nucleophile will be required in order to insure a particular product. However, in many instances subsequent reactions, such as hydrolysis, will lead to the same product irrespective of the particular nucleophile which was involved with the carbocation.

Depending upon the particular initiating group, certain types of catalysts will be preferred. Where a thioether is involved, such as a thioketal, metal halide Lewis acids are the preferred catalysts. With an oxyether, either protonic or metal halide Lewis acid type catalysts may be employed. Where a nitroalkane is employed as the nucleophile, normally protonic catalysts will be employed.

The concentration of the cyclization precursor can be varied widely, although relatively dilute solutions will be employed to minimize the opportunity for polymerization. Generally, the concentrations range from about 0.005 M to 0.5 M, more usually from about 0.001 to 0.1 M, and preferably from about 0.01 to 0.05 M. The acid concentration will vary depending upon the particular acid catalyst. With metal halide catalyst, a concentration may be as low as about 0.005 M, and will generally not exceed about 0.5 M, more usually being from about 0.01 to about 0.25 M. With protonic catalysts, the molarity may be substantially higher, usually being as high as 2 M, more usually up to about 1.5 M, and usually not less than about 0.1 M, more usually not less than about 0.2 M. Usually, there will be at least one equivalent of acid per mole of cyclization intermediate, generally not exceeding about 50 moles of acid catalyst per mole of cyclization precursor. The metal halide Lewis acids will generally have equivalent ratios of from about 1 to 10.

The nucleophile when used as an auxiliary with a solvent will generally be used in large molar excess in relation to the cyclization precursor. Normally, the nucleophile will be used in at least about 5 moles per mole of cyclization precursor and may be as high as 100 moles per mole or higher. Conveniently, the mole ratio of nucleophile to cyclization precursor will generally be from about 10–50:1.

Mild temperatures will normally be employed, generally not exceeding 10° C. and may be as low as −70° C., more usually being from about −50° C. to −10° C. The time will vary as required, generally being at least about 5 minutes and usually not exceeding about 24 hours, more usually being from about 15 minutes to about 200 minutes. The particular time will vary depending upon the stability of the final product, the time being chosen to optimize the yield.

IV. Tetracyclic Products

The tetracyclic products which are formed in accordance with this invention will have at least 23 carbon atoms, more usually at least 24 carbon atoms, and frequently at least 25 carbon atoms and generally not more than 35 carbon atoms, more generally not more than about 30 carbon atoms.

For the most part, the tetracyclic compounds formed by the subject cyclization will have the following formula:

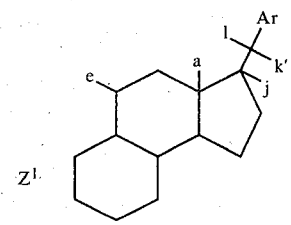

wherein:

a, e, j and Ar have been defined previously;

k' may be taken together with j to form a double bond or taken together with "1" to form oxo;

when not taken together with k', "1" may be halo, oxy, either hydroxy or hydrocarbyloxy, particularly alkoxy of from 1 to 6 carbon atoms, acylcarboxy particularly haloacylcarboxy and more particularly perhaloacylcarboxy, wherein the halo is of atomic number 9 to 17, aryl, alkenyl and hydroxyalkenyl, wherein the hydrocarbyl, acylcarboxy and hydroxyhydrocarbyl groups are of at least 1, usually at least 2, and not more than about 10 carbon atoms. For the most part, "1" will be halo, oxy or acylcarboxy; and $Z^1$ is a di- or trivalent organic radical which forms a ring of from 5 to 6 annular members with the carbon atoms to which $Z^1$ is attached and has from 0 to 2 chalcoxy groups or 0 to 1 oxo group and has from 1 to 2 sites of ethylenic unsaturation, there being one endo-double bond, which may be subsequently hydrogenated. When $Z^1$ is trivalent, there is a double bond to a bridgehead carbon atom. $Z^1$ is normally of from about 3 to 9 carbon atoms, usually of from 3 to 7 carbon atoms, and preferably of from about 4 to 7 carbon atoms and 0 to 2 chalcogen atoms.

Illustrative $Z^1$ groups include:
but-1-en-1,4-ylene;
3-methylprop-1-yl-3-ylidene;
2-(2'-thiolethylenethio)but-1-en-1,4-ylene;
3-isopropylidenebut-1-yl-4-ylidene;
3-ethylprop-1-yl-3-ylidene; and
3-oxobut-1-yl-4-ylidene.

When the cyclization is carried out employing a cyclohexenyl group as the initiator, the resulting product will for the most part have the following formula:

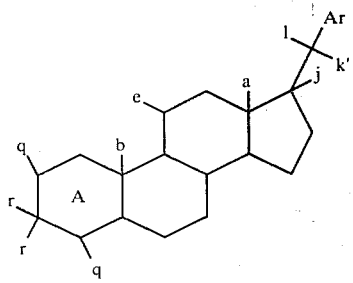

wherein:

all of the symbols have been defined previously with the exception of r and q;

one of the broken lines in the A ring is a double bond, particularly $\Delta^1$;

the q bonded to the ethylenic carbon atom is hydrogen or beta- or gamma-hydrochalcoxy-(OH or SH)-alkylenechalcoxy (alkylene of 2 to 3 carbon atoms), the other q is hydrogen; and the two r's are hydrogen or may be taken together to form alkylidene of from 1 to 4 carbon atoms, a cyclic oxy or thioketal or oxo.

When the cyclization is carried out with a cyclopentenol compound, the resulting product will for the most part have the following formula:

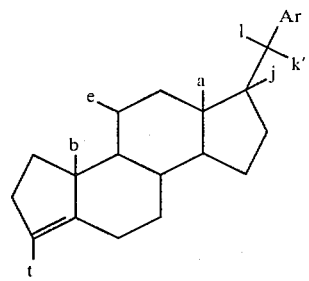

wherein: all of the symbols have been defined previously with the exception of t which is hydrogen or alkyl of from 1 to 4 carbon atoms, usually of from 1 to 2 carbon atoms, and preferably methyl.

Upon oxidation of the endocyclic double bond, for example, by ozonization, the A ring is opened to a diketone and if j and k' are taken together to form a double bond, that double bond is also cleaved to form the 17-one. The resulting product may be cyclized by base catalysis so as to form a cyclohexeneone A ring according to the following formulae:

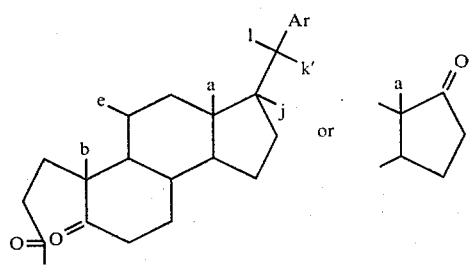

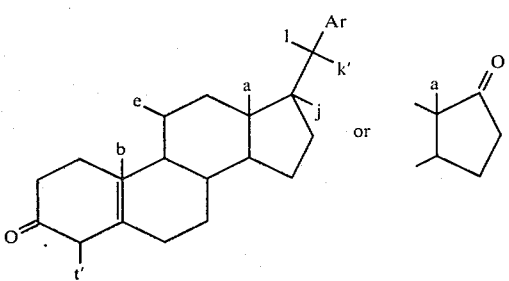

wherein: all of the symbols have been defined previously except for t', which is hydrogen or alkyl of from 1 to 3 carbon atoms, usually hydrogen or methyl.

Depending upon the other Z groups involved, various transformations of the functionalities present in the Z group will be appropriate. Ketones can be reduced to alcohols, double bonds introduced into the ring, exocyclic double bonds cleaved by ozonization and the like.

Where an alkyl substituent is present at the C-11, the product normally has the alpha-configuration as the major if not the sole product. The alpha-configuration at C-11 has been shown to have physiological activity in steroid derivatives. In addition, the intermediates can be resolved at an early stage, so that the alpha-C-11 isomer can be provided optically active.

EXPERIMENTAL

The following examples are offered by way of illustration and not by way of limitation. In order to avoid unnecessary repetition and undue extension of the application, where procedures were employed which were substantially the same for different compounds, only one procedure was described, and the amounts and yields reported for the other compounds. The differences in the procedure were primarily expedients which do not go to the operability of the procedure or to significant variation in the yield. Furthermore in many instances the procedures follow known reaction sequences, so that variations would be obvious to those skilled in the art.

(All temperatures not otherwise indicated are in Centigrade. All percents not otherwise indicated are by weight. The phrase "worked up in the usual manner" means the organic layer is washed with brine, dried over anhydrous magnesium sulfate, filtered, and the solvent removed in vacuo.)

EXAMPLE 1

3-Chloro-2-phenyltetrahydropyran

In a one liter 3-necked flask equipped with a fritted glass bubbler, thermometer and exit tube having a calcium chloride drying tube was introduced 118 g (128 ml, 1.4 mole) of dry dihydropyran and 400 ml of dry ether, the solution cooled with agitation to about $-30°$ with a dry ice-acetone bath and dried chlorine bubbled into the agitated solution at a rate such that the reaction temperature remained below $-10°$. The reaction was terminated when the solution turned yellow and a temperature drop was observed. A small portion of dihydropyran was added to the reaction mixture to remove the excess chlorine.

Into a dry flask fitted with dropping funnel reflux condenser, drying tube and mechanical stirrer was placed 51 g of magnesium turnings, followed by the addition of 200 ml of dry ether. A small portion of bromobenzene was added to initiate the reaction, followed by the remainder of 330 g (2.1 mole) of bromobenzene in 1 liter of dry ether at a rate sufficient to maintain reflux. The mixture was cooled in an ice-salt bath to which was added dropwise the cold ethereal solution of 2,3-dichlorotetrahydropyran. After completing the addition, the slurry was refluxed for 3 hours, cooled in an ice-water bath and 300 ml of cold 20 percent hydrochloric acid added slowly to the stirred mixture. The addition of 500 ml of water dissolved the precipitated salts, the layers were separated, the aqueous phase extracted with ether ($2 \times 200$ ml) and the combined ethereal layers washed with brine (200 ml) and dried over anhydrous potassium carbonate. In vacuo removal of solvent left an amber liquid which was distilled through a 20 cm Vigreux column, whereby 256 g was collected at 77°–90°/0.25 mm Hg. The product was redistilled at 153–154/16 mm Hg, the distillate crystallizing to give needles m.p. 39.5°–40.5°. The crude yield was 256 g (93% yield based on dihydropyran).

EXAMPLE 2 trans5-phenyl-4-penten-1-ol

Into a flask fitted with dropping funnel, mechanical stirrer and reflux condenser with nitrogen inlet was introduced 2 ml of dry xylene (a) and 69 g (3.0 g-atom) of sodium (b). The xylene was heated until the metal softened, the heating mantel removed, the flask briskly shaken to divide the sodium into sand-like particles and the flask allowed to cool. The xylene was removed and the sodium sand washed with dry ether ($3 \times 100$ ml) and the finely divided metal residue covered with 1.2 liters of dry ether (c). To the rapidly stirred suspension was added 256 g (1.3 mole) of 3-chloro-2-phenyltetrahydropyran (e) in 20 ml of ether (f). The addition was dropwise until the reaction began, as evidenced by a blue color and the remainder of the halide was added over 90 minutes. The resulting gray slurry was stirred, refluxed after one hour of addition, with the color changing to cream color and the reaction vessel then cooled in an ice bath and with rapid stirred 40 ml of ethanol followed by 9 ml of water were added cautiously. After separation of the layers, the aqueous phase was extracted with ether ($3 \times 200$ ml), the combined ethereal fractions washed with brine (200 ml) and dried over potassium carbonate. In vacuo removal of solvent left 219 g of a red liquid which was fractionally distilled and the fraction boiling at 94°–95°/0.18 mm Hg collected providing 61.5 g (29% yield).

EXAMPLE 3 trans-5-phenyl-4-pentenal

To a dry 3 liter 3-necked flask equipped with mechanical stirrer, thermometer and nitrogen inlet was added 1.5 liter of dry dichloromethane (a) and 95 g of dry pyridine (b). The stirred solution was cooled ot an internal temperature of 5° and 60 g of chromium trioxide (c) was added in one portion. The mixture was stirred an additional 5 minutes and then allowed to warm to 20° over 60 minutes, giving a solution of Collins reagent. A solution of 16.2 g of trans-5-phenyl-4-penten-1-ol (d) in 100 ml of dry dichloromethane (e) was then added rapidly. The mixture was stirred an additional 15 minutes and then decanted from the residue. The residue, a black tar, was washed with ether ($3 \times 500$ ml) and the combined organic solution was worked up in the usual manner. Evaporation of the solvent gave the aldehyde (15 g) as a pale yellow liquid. TLC; silica gel HF$_{254}$; ethyl acetate/benzene 1:9 R$_f$ 0.50.

EXAMPLE 4 trans-2-methyl-7-phenyl-1,6-heptadien-3-ol

Magnesium (a) (12.5 g) was flame dried in a 250 ml 3-necked flask equipped with mechanical stirrer, reflux condenser, and addition funnel. The magnesium was covered with 52 ml of dry tetrahydrofuran (b) and reaction was initiated by the addition of ca. 0.5 ml of ethylene dibromide under a nitrogen atomosphere. To the stirred mixture was added 30.9 g of 2-bromopropene (c) dropwise at a rate which maintained reflux without external heating. After the addition, the Grignard solution was stirred until it had cooled to room temperature (0.5–1 hour) and then cooled to $-15°$. Then 27.35 g of trans-5-phenyl-4-pentenal (d) was added dropwise over 15 minutes. After the resultant green mixture was stirred at room temperature for 2 hours, 130 ml of a saturated solution of ammonium chloride was added followed by 200 ml of water. The layers were separated and the aqueous portion extracted with ether ($3 \times 200$ ml). The organic layer were worked up in the usual manner to give after evaporation, the alcohol as an orange liquid (33 g). TLC; silica gel HF$_{254}$; ethyl acetate/benzene 2:8 R$_f$ 0.45.

EXAMPLE 5 methyl trans,trans-4-methyl-9-phenyl-4,8-nonadienoate

In a 250 ml acid-washed round-bottom flask was placed 33.2 g of the above crude alcohol (a), 120.2 g of trimethylorthoacetate (b) and 1.18 g of propanic acid (c). The flask was fitted with a condenser and a Dean Stark trap with heating tape and the reaction mixture was stirred under nitrogen in a 105° (d) oil bath for 19 hours (e). The dark yellow reaction mixture was cooled, poured onto 150 ml of water, and extracted with ether (4×100 ml). The combined ethereal solution was washed with 1.2 N hydrochloric acid (3×100 ml) and worked up as usual to afford 37.8 g of an orange liquid. The crude ester was purified by distillation bp 110°–114°/0.02 mm. TLC; silica gel $HF_{254}$; ethyl acetate/benzene 1:9 $R_f$ 0.61.

EXAMPLE 6 trans,trans-4-methyl-9-phenyl-4,8-nonadien-1-ol

To an oven-dried, 250 ml round-bottom flask fitted with addition funnel and magnetic stirrer was added 6.2 ml of Red-al (a) and 58 ml of dry tetrahydrofuran (b). The reaction vessel was cooled on an ice-water bath, and to the stirred solution was added over 5 minutes a solution of 5.0 g of the above mentioned diene ester (c) in 10 ml of dry tetrahydrofuran (d). The colorless solution was stirred under nitrogen for 2 hours in the cold and then the excess hydride was destroyed by carefully adding 5% sodium hydroxide solution until a white precipitate and clear supernatant resulted. The liquid was decanted and the aluminium salts washed with ether. The tetrahydrofuran volume was reduced by evaporation to ca. 20 ml and diluted with 60 ml of ether. The combined organic solution was worked up in the usual manner affording the alcohol as a pale yellow liquid (4.5 g). TLC; silica gel $HF_{254}$; ethyl acetate/benzene 2:8 $R_f$ 0.34.

EXAMPLE 7 trans,trans-4-methyl-9-phenyl-4,8-nonadienal

Following the procedure given for the synthesis of trans-5-phenyl-4-pentenal (Ex. 1), 4.3 g of the above mentioned alcohol (a) was converted using 18 g of pyridine (b) and 11.4 g of chromium trioxide (c) to 3.95 g crude aldehyde. This crude aldehyde was chromatographed over Florisil. Elution with dichloromethane gave 3.6 g of pure aldehyde. TLC; silica gel $HF_{254}$; ethyl acetate/benzene 1:9 $R_f$ 0.58.

EXAMPLE 8

6-methyl-1-phenyl-12-(2'-methyl-4'-oxo-2'-cyclohexenyl)-trans,trans,trans-1,5,9-dodecatriene ethylene thioketal In an oven-dried, 250 ml round-bottom flask equipped with mechanical stirrer was placed 7.3 g of the phosphonium salt (3-(4',4'-ethylenedithio-2'-methylcyclohex-2'-en-1'-yl)propyl triphenylphosphonium iodide) (a). After flushing the flask with dry nitrogen, 22.8 ml of dry tetrahydrofuran (b) was added and the tan-colored suspension was stirred at 27° under nitrogen. Phenyl lithium in tetrahydrofuran was slowly added via syringe until a permanent yellow color was obtained indicating a small concentration of the phosphorous ylid. Then one equivalent of phenyllithium in tetrahydrofuran was added. Complete dissolution to a clear cherry-red color occurred within one minute. The solution of the ylid was then cooled to −70° and after stirring for 15 minutes, a solution of 2.70 g of the above aldehyde (c) in 2.5 ml tetrahydrofuran was added dropwise. The color of the solution lightened to pale orange as it was stirred for an additional 15 minutes. Then 15.1 ml (d) of 1.02 M (e) phenyllithium in tetrahydrofuran was added generating a very dark-red solution of the betaine ylid. Dry ether (55 ml) was added to adjust the THF/ether ratio 1:1. The temperature of the cooling bath was adjusted to −30° and the reaction mixture was stirred for 10 minutes at this temperature before the ylid was quenched by the dropwise addition of 10 ml of methanol. The resultant pale tan mixture was brought to 27° and dissolution occurred to give a yellow-orange solution which was stirred overnight.

The reaction mixture was poured into 300 ml of hexane and after a few minutes stirring the precipitated triphenylphosphine oxide was filtered. The solid residue was washed with ether (2×50 ml) and the combined organic solution evaporated under reduced pressure to afford 4.6 g of an orange oil. The crude product was purified by chromatography on Florisil. Elution with 5% ether-hexane gave the thioketal as an oil (3.4 g). TLC; silica gel $HF_{254}$; ethyl acetate/benzene 1:9 $R_f$ b 0.75 ether/hexane 1:4 $R_f$ 0.55.

EXAMPLE 9

6-methyl-1-phenyl-12-(2'-methyl-4'-oxo-2'-cyclohexenyl)-trans,trans,trans-1,5,9-dodecatriene In a round-bottom flask equipped with condenser, magnetic stirrer, and nitrogen inlet are placed 3.4 g of the thioketal mentioned above (a), 97.5 ml of acetonitrile (b) and 19.5 ml of water (c). The resultant solution was deaerated and 11.1 ml of iodomethane (d) was added. The reaction mixture was then stirred under nitrogen at 45° for 12 hours. The flask stood at room temperature overnight and then the yellow mixture was poured into 200 ml of ether. The solution was washed with a 10% solution of sodium thiosulphate (2×200 ml) and the aqueous layers extracted back with ether (3×150 ml). The combined organic solution was then worked up as usual. The resultant yellow oil was purified by chromatography on Florisil. Extraction with ether/hexane 1:9 gave 2.3 g of the enone as a pale yellow liquid. TLC; silica gel $HF_{254}$; ethyl acetate/benzene 1:4 $R_f$ 0.55.

EXAMPLE 10

6-methyl-1-phenyl-12-(2'-methyl-4'-hydroxy-2'-cyclohexenyl)-trans,trans,trans-1,5,9-dodecatriene In an oven-dried, 25 ml round-bottom flask was placed 0.98 g of the above enone (a) and 9 ml of dry tetrahydrofuran (b). The flask was equipped with a magnetic stirrer, serum cap, and nitrogen inlet, and then cooled to 0°. A solution of 0.69 ml of Red-al (c) in 4 ml of dry tetrahydrofuran (d) was added slowly via syringe and the solution was stirred for 1.5 hours at 0° under nitrogen. The excess hydride was quenched by careful addition of 5% sodium hydroxide solution until a precipitated appeared. The clear liquid was decanted and the aluminium salts washed with ether. The organic solution was then worked up in the usual manner affording 0.975 g of an oily mixture of the two alcohols. They were purified by chromatography on basic alumina (activity 4). Elution with ether/hexane 1:9. TLC; silica gel $HF_{254}$; ethyl acetate/benzene 1:4 $R_f$ 0.41.

EXAMPLE 11

$\Delta^1$-17-($\alpha$-hydroxybenzyl)-5$\beta$-androstene

In a flame dried, 250 ml 3-necked flask fitted with mechanical stirrer, serum cap and nitrogen inlet was placed 33 ml of dry dichloromethane (a) and 0.49 ml of trifluoroacetic acid (b). The solution was cooled to −25° and deaerated thoroughly. To the well stirred solution was added over 10 minutes a solution of 0.238 g of the above mentioned mixture of allylic alcohols (c) in 1 ml of dry dichloromethane (d). Two 0.5 ml washings were also added. The reaction turned orange after ca. 15 minutes at −25° and became darker with time. Stirring at −25° (e) under nitrogen was continued for 22 hours (f) at which time the dark red reaction was quenched by the addition of 50 ml of saturated sodium bicarbonate solution and 50 ml of ether. The color faded immediately. The layers were separated and the aqueous phase extracted with ether (2×25 ml). The combined organic solution was washed with water (50 ml) and brine (50 ml), dried over magnesium sulphate, filtered, and finally concentrated under reduced pressure leaving 0.299 g of a pale yellow liquid. The crude product was then hydrolysed directly by dissolution in 24 ml of methanol, 4 ml ether and 9.5 ml of water. The cloudy mixture was deaerated and 0.78 g of potassium carbonate was added. The mixture was then stirred at room temperature under nitrogen for 20 hours. The reaction mixture was concentrated at reduced pressure and poured onto ether. The layers were separated and the aqueous phase extracted with ethyl acetate (4×10 ml). The usual workup of the organic extract gave 0.231 g of a pale yellow foam. This product was purified by chromatography on Florisil. Elution with 3% ether-hexane gave 55 mg of $\Delta^1$-17$\beta$-($\alpha$-hydroxybenzyl)-5$\beta$-androstene. TLC; silica gel HF$_{254}$; ethyl acetate/benzene 1:9 R$_f$0.62. Elution with 6% ether-hexane yielded 100 mg of $\Delta^1$-17$\beta$-($\alpha$-hydroxybenzyl)-5$\beta$-androstene. TLC; silica gel HF$_{254}$; ethyl acetate/benzene 1:9 R$_f$0.42.

The following table indicates the amounts of materials, in some instances also, conditions yield, and a thin layer chromatographic conditions for the tolyl, anisyl, naphthyl and acetylenic analogs of the styryl terminating group. The small letters which are found in the foregoing examples indicate the materials to which the amounts refer. The numbers are in the same dimensions as the numbers set forth in the Examples. The reactions begin with dihydropyran and end with the cyclization to the steroid nucleus.

TABLE I

| X* | a | b | c | d | e | f | Yield | m.p. | Eluens | Rf |
|---|---|---|---|---|---|---|---|---|---|---|
| I | | | | | | | | | | |
| p-Me | 11 | 40 | 5.1 | 60 | 34+ | 60 | 23.3 | | | |
| p-OMe | 11 | 40 | 5.1 | 60 | 34.4++ | 60 | 24.2 | | | |

*X
p-Me - p-tolylethenyl
p-OME - p-anisylethenyl
1-naphtyl - 1-naphtylethenyl
ethinyl - phenylethinyl
+ -p-bromotoluene
++ p-bromoanisole

| X | a | b | c | d | e | f | Yield | m.p. | Eluens | Rf |
|---|---|---|---|---|---|---|---|---|---|---|
| II | | | | | | | | | | |
| p-Me | 17 | 0.5 | 63 | 100 | | | 37 | | | |
| p-OMe | 5 | 0.25 | 22.2 | 50 | | | 14.1 | | | |
| III | | | | | | | | | | |
| p-CH$_3$ | 2 | 138 | 85 | 25 | 100 | | 21.8 | | Hex/Et$_2$o1:1 | 0.5 |
| p-OMe | 0.9 | 82 | 51 | 14 | 50 | | 11.3 | | Hex/Et$_2$o1:1 | 0.5 |
| IV | | | | | | | | | | |
| p-CH$_3$ | 8 | 100 | 18.2+ | 22++ | | | 22.9 | | Hex/Et$_2$o1:1 | 0.6 |
| p-OMe | 4 | 50 | 9.1+++ | 11++ | | | 11.9 | | Hex/Et$_2$o1:1 | 0.6 |
| ethinyl | 1.6 | 50 | 7.65* | 5++ | | | | | | |

+diluted w/30ml THF
++diluted w/50ml THF
+++diluted w/15ml THF
*diluted w/150ml THF

| X | a | b | c | d | e | f | Yield | m.p. | Eluens | Rf |
|---|---|---|---|---|---|---|---|---|---|---|
| V | | | | | | | | | | |
| p-Me | 20 | 67+ | 0.42 | 143 | 2.5 | | 24.6 | | Hex/Et$_2$o1:1 | 0.8 |
| p-OMe | 11.5 | 33.5+ | 0.21 | 145 | 2.5 | | 13.6 | | Hex/Et$_2$o1:1 | 0.8 |
| 1-naphthyl | 3.4 | 16.2 | 0.14 | 105–110 | 20 | | 3.3 | | Hex/Et$_2$o1:1 | 0.7 |
| ethinyl | 5.7 | 100++ | 0.50 | 95 | 24–48 | | 6.85 | | | |

+triethylorthoacetate
++ml

| X | a | b | c | d | e | f | Yield | m.p. | Eluens | Rf |
|---|---|---|---|---|---|---|---|---|---|---|
| VI | | | | | | | | | | |
| p-Me | 20 | 75 | 5.5 | 20 | | | | | Pent/Et$_2$o1:1 | 0.5 |
| p-OMe | 7 | 50 | 2.0 | 10 | | | 1.5 | | Pent/Et$_2$o1:1 | 0.5 |
| 1-naphthyl | 14 | 50 | 3.2 | 20 | | | 1.3++ | | Pent/Et$_2$o1:1 | 0.5 |
| ethinyl | 1 | 200 | 6.7 | 50 | | | 4.8 | | 4%Et$_2$0/OH+ | |

+Florisil
+ + Yield improved using LAH as reducing agent
+ + +LAH used as reducing agent; reaction at room temp.

| X | a | b | c | d | e | f | Yield | m.p. | Eluens | Rf |
|---|---|---|---|---|---|---|---|---|---|---|
| VII | | | | | | | | | | |
| p-Me | 3.9 | 15.6 | 10 | | | | 3.47 | | Hex/Et$_2$o1:1 | 0.6 |
| p-OMe | 3.6 | 8.2 | 1.4 | | | | 1 | | Hex/Et$_2$o1:1 | 0.6 |
| 1-naphthyl | 1.25 | 4.2 | 2.7 | | | | 1.1 | | Hex/Et$_2$o1:1 | 0.8 |
| ethinyl | 1.6 | 8.85 | 5.6 | | | | 1.4 | | | |
| VIII | | | | | | | | | | |
| p-Me | 1.18 | 10 | 0.5 | 0.9 | 2.8 | | 0.70 | | | |
| p-OMe | 1.25 | 10 | 0.57 | 1 | 2.5 | | 0.68 | | | |
| 1-naphthyl | 2.21 | 10 | 1 | 1.45 | 2.5 | | 1.3 | | | |
| ethinyl | 0.19 | 10 | 0.70 | 0.60 | 0.74 | | | | | |

IX

TABLE I-continued

| | a | b | c | d | | | Yield | m.p. | Eluen | Rf |
|---|---|---|---|---|---|---|---|---|---|---|
| p-Me | 1 | 30 | 6 | 10 | | | 0.7 | | Hex/Et₂o1:1 | 0.5 |
| p-OMe | 0.6 | 20 | 4 | 8 | | | 0.41 | | — | |
| 1-naphthyl | 1.2 | 30 | 8 | 10 | | | 0.94 | | Hex/Et₂o1:1 | 0.5 |
| ethinyl | 0.80 | 5 | 1 | 0.5 | | | 0.50 | | 5%EtoAc/φH | 0.3 |
| X | | | | | | | | | | |
| p-Me | 0.42 | 5 | 0.5 | 3 | | | 0.40 | | Hex/Et₂o1:1 | 0.4 |
| p-OMe | 0.37 | 4 | 0.4 | 3 | | | 0.31 | | — | |
| 1-naphthyl* | 0.64 | 6 | 2 | 5 | | | 0.51 | | Hex/Et₂o1:1 | 0.4 |

*inverse addition

| X | a | b | c | d | e | f | Yield | m.p. | Eluen | Rf |
|---|---|---|---|---|---|---|---|---|---|---|
| XI | | | | | | | | | | α-0.8 |
| p-Me | 10 | 0.21 | 0.11 | 1.2 | −50 | 0.5 | 83 | | 25% EtoAc/Hex | β0.6 |
| p-OMe | 5 | 0.14 | 0.075 | 1.5 | −50 | 0.5 | 17 | | Hex/Et₂o1:1 | 0.7 |
| 1-naphthyl | 40 | 0.63 | 0.35 | 4 | −50 | 0.5 | 305 | | Hex/Et₂o1:1 | 0.8 |
| XII | | | | | | | | | | |
| p-OMe | 5 | 0.5 | 0.04 | | | | 11.2 | | Hex/Et₂o1:1 | 0.8 |
| α-1* | 75 | 2 | 0.2 | | | | 65.1 | 140–142 | Hex/Et₂o1:1 | 0.8 |
| β-1* | 150 | 4 | 0.4 | | | | 132 | 156–158 | Hex/Et₂o1:1 | 0.8 |

*naphthoyl

The procedure for preparing the initial intermediates in the naphthyl series differ from the procedures employed for the other analogs. The following examples set forth the alternative procedure for the naphthyl series.

EXAMPLE 12

1-α-naphthyl-2-propen-1-ol

To a solution of vinyl lithium (2.04 g, 0.06 mole, 2.5 ml) in dry THF (30 ml) under N₂ with stirring, at −60° was added dropwise a solution of naphthaldehyde (4.68 g, 0.03 mole) in 10 ml THF. The reaction was kept at −60° for 30 min, the flask was then warmed to room temperature and 5 ml MeOH added cautiously with rigorous stirring, followed by 100 ml of ether. The ethereal solution was washed with brine and dried over MgSO₄. After evaporation of the solvent, the residue was chromatographed through Florisil (250 g), eluted first with hexane and then a mixture 20% ether in hexane, giving the expected product. 4.77 g (86% yield). b.p. 92–105°/10μ.

EXAMPLE 13 trans-2-methyl-7-naphthyl-1,6-heptadien-3-ol

A solution of the above alcohol (4.5 g, 0.024 mole) and 2,4 dinitrophenol (4.5 g, 0.024 mole) in 25 ml toluene was treated with 3,3-dimethoxy-2-methyl-1-butene (6.24 g, 0.048 mole) in 25 ml toluene. The mixture was placed in an oil bath 105°–110° fixed with a Dean-Stark trap and a condenser and stirred. After 8 hours, 6.24 g (2 mol equivalent) of additional acetal was added to the reaction mixture, and the mixture stirred and heated for an additional 17 hours. The material was then poured through 300 g Florisil column, eluted with 20% ether in hexane. After chromatographing 6 g (98% yield) of the expected ketone was obtained. IR 1679 (C=O) R$_f$0.7.

To the above product (6 g, 0.024 mole) in 20 ml ethanol was added dropwise a solution of NaBH₄ (2 g, 0.052 mole) in 10 ml ethanol at 0°, with continuous stirring for an hour. A saturated solution of NH₄Cl was added to destroy the excess of reducing agent and the mixture extracted with ether and the ethereal solution worked up in the usual manner. After evaporation of the solvent, a yellow oil residue was chromatographed through a Florisil column (200 g) and eluted with 10% ethanol in hexane, then distilled to yield 3.450 g, 56% yield (based on the alcohol) b.p. 120°–137°/5μ. Analysis by TLC eluted with ether-hexane (1:1) gave R$_f$0.8.

The next example, Example 14, indicates the preparation of a precursor to 5-phenyl-4-pentynal.

EXAMPLE 14

5-ethylenedioxy-1-phenylpentyne

In an oven dried 500 ml 3-necked flask equipped with a nitrogen inlet, serum cap and a magnetic stirrer was dissolved 7.5 g (73.5 mmol) of phenyl acetylene in 250 ml of freshly dried and distilled dimethoxyethane. This solution was cooled to 0° and 73.2 ml hexamethylphosphoramide which was freshly distilled from sodium metal was added via syringe. Maintaining the solution at 0°, 35 ml of 2.1 M n-butyl lithium solution in hexane (73.5 mmol) was added in a similar fashion. After 10 minutes of stirring, the serum cap was replaced with an addition funnel, and (13.4 g, 973.5 mmol) of the ethylene glycol acetal of 3-bromopropanol dissolved in 50 ml of dimethoxyethane was added. After an additional 1 hour of stirring, thin layer analysis showed that all the bromoacetal was consumed. The reaction was quenched with water and the resulting mixture was partitioned between ether and water. The aqueous layer was further extracted twice with ether. The organic layers were combined, washed twice with water, once with brine and dried. Removal of the solvents on a rotary evaporator followed by distillation afforded 9.15 g (62%) of ketal: b.p. 120°–125° (0.2 mm).

Rather than employing a cyclohexenone initiator the initiator can be a cyclopentenol. The following examples exemplify the preparation of a cyclopentenol initiator and its use in cyclization.

EXAMPLE 15

5,8-bis(ethylenedioxy)nonyltriphenylphosphonium iodide

A solution of 4.13 g (11.2 mmol) of 5,8-bis(ethylenedioxy)nonyl iodide and 2.93 g (11.2 mmol) of triphenyl phosphine in 25 ml of acetonitrile was buffered with a few drops of Hunig's Base and heated under nitrogen at 65° for 24 hours. The solvent was removed in vacuo until the resulting gum began to foam. This viscous gum was taken up in 25 ml of 3-pentanone and the resulting solution was seeded with a crystal of the salt and allowed to stand until crystallization was complete. Filtration afforded 4.98 g of salt. The mother liquors were placed in the freezer overnight and another 0.64 g of salt crystallized. Yield (5.62 g, 80%).

EXAMPLE 16

1-phenyl-6-methyl-14,17-bis(ethylenedioxy)octadeca-trans,trans-5,9-dienyne-1

In an oven dried cylindrical reaction vessel fitted with an addition funnel, serum stopper, and a mechanical stirrer which allowed for the introduction of argon through the bottom of the shaft was placed 4.10 g (6.5 mmol) of the above phosphonium salt. The salt was pumped down at 0.5 mm for 90 min, and then placed under an argon atomsphere, introduced through the stirring shaft. The salt was slurried in 10 ml of freshly dried and distilled THF. One drop of a 2.5 M solution of phenyllithium in THF produced a lasting ylide color. A total of 2.5 ml (6.25 mmol) of phenyllithium solution was then added via syringe, and the resulting cherry-red solution was stirred at 23° for 5 min and then cooled at −78° and stirred an additional 10 min. A solution of 1.4 g (6.2 mmol) of 4-methyl-9-phenyl-trans-non-4-en-8-ynal in 5 ml of THF was then added dropwise thhrough the addition funnel so that it ran down the flask wall. Addition lasted 20 minutes and was followed by an additional 2 ml of THF to wash the flask wall. The now orange solution was stirred for 15 min after which another 3 ml of phenyllithium solution was added via syringe down the flask wall. The resulting dark red solution was then diluted with enough freshly dried and distilled ether (23 ml) to make the solvent 50% ether. This dilution was accomplished in the same fashion as the aldehyde addition. The cooling bath temperature was raised to −25° and stirring continued for 30 min at which time the reaction was quenched by addition of excess methanol. The cooling bath was removed and stirring continued overnight. The products were partitioned between ether and water, and the organic fraction worked up in the usual fashion. The resulting oil was chromatographed on 80 g of Florisil. After elution with hexane and 5% ether/hexane, a 10% ether/hexane mixture eluted 2.07 g (73%) of the bisketal product as an oil which displayed one peak on vpc (6', 3% OV-17, 240°), rt=30 min. A sample of this oil was distilled bulb-to-bulb; b.p. 210° (15μ).

EXAMPLE 17

1-phenyl-6-methyl-14,17-dioxo-octadeca-trans, trans-5,9-dienyne-1

A solution of 900 mg (1.00 mmol) of the above bisketal in 60 ml of methanol and 15 ml of 5% hydrochloric acid was stirred at room temperature for 18 hours. The solution was diluted with 30 ml of water and extracted with four 30 ml portions of ether. These extracts were combined, washed with saturated sodium bicarbonate solution, and worked up in the usual fashion. The resulting oil was chromatographed on 50 g of Florisil. Elution with 500 ml of a gradient from benzene to 20% ether/benzene afforded 675 mg (93%) of an oil, the bisketone product, which displayed one peak on vpc (6', 3% OV-17, 240°), rt=11.5 min. A sample of this oil was distilled bulb-to-bulb: b.p. 200° (20μ).

EXAMPLE 18

1-phenyl-6-methyl-12(2-methyl-5-oxocyclopentenyl)-dodeca-trans,trans-5,9-dienyne-1

A solution of 650 mg (1.79 mmol) of bisketone (Ex. 17) in 30 ml of methanol and 5 ml of 5% of 5% potassium hydroxide was refluxed under argon for 24 hours. The solution was diluted with 20 ml of water and extracted with three 40 ml portions of ether. These extracts were combined, washed with water, and worked up in the usual fashion. The resulting oil was chromatographed on 50 g of Florisil. Elution with 400 ml of a gradient from benzene to 20% ether/benzene produced 410 mg of an oil which displayed one peak on vpc (6', 3% OV-17, 238°) rt=15.5 min. Bulb-to-bulb distillation afforded 383 mg (58%) of the cyclopentenone product as an oil: b.p. 200° (7μ).

EXAMPLE 19

Preparation and cyclization of 1-phenyl-6-methyl-12-(2',5'-dimethyl-5'-hydroxycyclopentenyl)dodeca-trans,trans-5,9-dienyne-1

An ice cold solution of 200 mg (0.58 mmol) of cyclopentenone (Ex. 18) in 20 ml of ether was treated with 0.6 ml of 1.5 M methyl lithium solution. After 10 min of stirring, the reaction was quenched with saturated sodium sulfate solution, dried over anhydrous potassium carbonate, and filtered through a plug of glass wool into a cold flask. The solvent was removed on a rotary evaporator at 0°. Meanwhile, a solution of 800 mg of ethylene carbonate and 1.4 ml of trifluoroacetic acid in 26 ml of olefin free $CH_2Cl_2$ was cooled under argon to −45°. The alcohol was taken up in 14 ml of cold $CH_2Cl_2$ and added dropwise, via syringe, to the acid solution. After addition was complete, stirring was continued at −45° for 45 min., whereupon the reaction was quenched with 14 ml of methanol and 6 ml of 5% sodium hydroxide solution. Stirring was continued overnight at room temperature. The mixture was diluted with ether, washed with water, then worked up in the usual fashion. The resulting oil was chromatographed on 100 g of Florisil in a tapered column. Elution with 5% ether/hexane provided three fractions with significant material in them. The first fraction was 32.8 mg of a single material (rt=7 min, 6' 3% OV-17, 238°) assigned as cis fused ketone. The compound crystallized on standing, and after two recrystallizations from ethanol, had m.p. 122°–125°.

The second fraction obtained was 80.4 mg of a mixture of the above ketone, the cis fused ketone and two trans-fused C-17 epimeric ketones.

The third fraction obtained was 52.2 mg of a single compound (rt=11 min, 6' 3% OV-17, 238°) assigned as the trans-fused β-epimer ketone. The compound crystallized on standing and after two recrystallizations from ethanol had m.p. 108°–111°.

Once the polyunsaturated precursor has been cyclized the resulting nor-steroid or steroid may be modified in a number of ways to prepare steroids having known physiological activity. The following reactions are illustrative of such modifications.

EXAMPLE 20

17-(α-hydroxybenzyl)-5β-androstane

To 43 mg (0.118 mmole) of $\Delta^1$-17α-(α-hydroxybenzyl)-5β-androstene in 1 ml of ethyl acetate was added a small quantity of deactivated Raney nickel in 1 ml of ethanol. The mixture was stirred for 30 minutes, filtered through a Celite pad, and the solvent evaporated under reduced pressure leaving a white crystalline material. A hydrogenation flask was charged with 6 ml of an ethanol solution containing the above solid, 1 mg of platinum oxide (Engelhard), and an ethanol rinsed magnetic stirring bar. The system was deaerated flushed with hydrogen (4x) and the mixture stirred under a hydrogen atmosphere for 0.5 hour. After filtering the mixture through a Celite pad, the solvent was removed under reduced pressure, leaving 42 mg (98% yield) of a slightly cloudy liquid. A sample was purified by chromatography on Florisil, eluted with hexane, 1%, and 3% solutions of ether in hexane. The resultant colorless oil was then recrystallized twice from hexane to afford white rosettes, m.p. 129°–130°. The process was repeated for the 17β-epimer.

EXAMPLE 21

17-benzoyl-5β-androstane

The procedure described was employed for both epimers. In a 10 ml round-bottom flask equipped with magnetic stirrer and nitrogen inlet was placed 42 mg (0.115 mmole, nominal) of the above crude alcohol (Ex. 20), and 2.5 ml of acetone, the solution stirred under nitrogen, cooled to 0° and deaerated. The cooling bath was adjusted to 5°–10° and 0.045 ml (0.12 mmole) of Jones reagent (vide supra) was added over 2 minutes, the reaction mixture stirred for an additional 15 minutes and then isopropanol added to destroy excess chromic acid. After diluting the reaction mixture with 2 ml of water, 2 ml of brine and 2 ml of ether and stirring for a few minutes, the layers were separated and the aqueous phase extracted with ethyl acetate. The organic layers were combined, washed with 1:1 5% sodium hydroxide-brine solution followed by brine washing, filtered, and concentrated under reduced pressure to afford 40 mg (96% yield) of crystalline product. Recrystallization (3x) from ethanol afforded colorless needles, 17α m.p. 165°–180°; 17β m.p. 189.5°–191°.

EXAMPLE 22

17-hydroxy-5β-androstane

A 32 mg (0.0876 mmole) sample of each epimeric ketone (Ex. 21) was dissolved in separate flasks each containing 1 ml of dry dichloromethane, 191 mg (1.31 mmole) of oven-dried dibasic sodium phosphate added and then cooled to 0°. In a third flask was prepared a solution of peroxytrifluoroacetic acid by the addition of 0.024 ml of 90% hydrogen peroxide and 0.146 ml of trifluoroacetic anhydride to 1 ml of dry dichloromethane at 0° followed by stirring for 0.5 hour. One-half ml (0.45 mmole peracid) of this solution was then added via syringe to each of the above cold, stirred slurries. The reaction mixtures were allowed to warm to room temperature, sealed with glass stoppers, and stirred in the dark for 11 days. On the fourth and eighth days of reaction, another 0.45 mmole portion of the peracid, prepared as above, was added to each reaction mixture. After 11 days, the reactions were worked up independently by pouring the mixtures onto 5 ml of water overlaid with 5 ml of ethyl acetate. The layers were separated and the aqueous phase extracted with ethyl acetate (3×3 ml). The combined organic layers in each case were then worked up as usual leaving yellow liquids. The crude esters were then cleaved by stirring each sample in 1 ml of dry ether at 0° with 2 spatula tips of lithium aluminum hydride for 45 minutes. Excess hydride was decomposed by cautiously adding 5% sodium hydroxide solution. The white precipitates were filtered and washed with portions of ether. The organic layers were then dried over magnesium sulfate, filtered, and concentrated under reduced pressure affording the products as colorless liquids. The crude products were then purified by preparative TLC using continuous elution technique for 1.25 hours with 30% ethyl acetate in hexane as eluant. The bands were visualized by searing with a hot wire.

Chromatography afforded two bands of material in the case of each product. The less polar band from the reaction product of the β-ketone (5 mg) was one peak by vpc on 3% XE-60 at 250°, rt=4.0 min. The lower band (7 mg) was two components by vpc, rt=3.0 and 5.0 minutes, on 3% XE-60 at 200° in a 2:1 ratio. The less polar band from the reaction product of the α-ketone afforded 13 mg of a colorless liquid which by vpc on 3% XE-60 at 250° was one component, rt=3.8 minutes. The lower $R_f$ band from this chromatography afforded 7 mg of material which contained 2 components by vpc on 3% XE-60 at 200°, rt=2.7 and 4.7 minutes, in a ratio of 2:1. Neither of these components coinjected with either of the two compounds obtained from the lower $R_f$ band of the β-series chromatography.

EXAMPLE 23

5β-androstan-17-one

The above mixture of alcohols (ca. 12 mg) was dissolved in 1 ml of acetone. The solution was cooled to 0° and deaerated with nitrogen. The bath temperature was brought to 5°–10° and then 5 drops of Jones reagent (vide supra) was added to the rapidly stirred mixture under nitrogen. The reaction mixture was stirred for 20 minutes and the excess Jones reagent was decomposed with a little isopropanol. The reaction mixture was diluted with water and brine, and then ether added. The layers were separated and the aqueous phase extracted with ethyl acetate. The combined organic solution was then washed with 1:1 5% sodium hydroxide-brine solution followed by brine. Drying over magnesium sulfate, filtration, and removal of solvent under reduced pressure gave 12 mg of a yellow liquid. Analysis by vpc on 3% XE-60 at 200° showed only one component, rt=3.1 minutes. The crude oil was chromatographed on 1 g of Florisil, eluted with hexane and 2%, 4%, and 6% solutions of ether in hexane. A total of 4 mg of colorless oil was collected. The synthetic steroid was recrystallized twice from ethanol to afford white needles, m.p. 98°–100°.

EXAMPLE 24

$\Delta^1$-17-(-α-and β-p-toluoyl)-5β-androstene

In a 10 ml round-bottom flask equipped with magnetic stirrer and nitrogen inlet, was placed 36 mg (0.095 mmoles) of the crude alcohol ($\Delta^1$-17-(α-hydroxy-p-methylbenzyl)-5β-androstene) dissolved in dry acetone (2 ml). Then the Jones reagent (0.030 ml; 0.08 mmoles) was added dropwise. The reaction mixture was stirred at room temperature for 15 minutes, then titrated with isopropanol to destroy excess of chromic acid. The reaction mixture was diluted with 1 ml of water and then extracted with ether (3×10 ml), after usual workup and removal of solvent, it afforded 28 mg of a yellow oil, which was chromatographed by preparative TLC eluted with hexane/ether 1:1 $R_f$=0.8.

EXAMPLE 25

4,5-seco-3,5-dioxo-17β-benzoylandrostane

A solution of 90 mg (0.25 mmol) of the trans-fused C-17β epimer prepared above (recrystallized from hexane) in 3 ml of methylene chloride and 3 ml of methanol (freshly distilled from magnesium methoxide) was cooled to −78° with stirring. Ozone was then bubbled through the solution for five minutes or until the color of the solution turned blue. The excess ozone was removed by bubbling argon through the solution. The resulting colorless solution was then treated with 160 mg (2.4 mmol) of zinc dust and 9 ml of acetic acid and stirred at 0° for 1 hour and at room temperature for 3 hours. The suspension was diluted with water and extracted twice with ether. The ether extracts were washed three times with saturated sodium bicarbonate solution and worked up in the usual fashion.

EXAMPLE 26

17α- and 17β-Benzoylandrost-4-ene-3-one

To the crude triketone prepared above was added 10 ml of methanol and 5 ml of methanolic 5% KOH. The solution was stirred under argon for 40 hours. The faint yellowish solution was siluted with water and extracted twice with ether. The ether extracts were washed twice with saturated sodium bicarbonate solution and worked up in the usual fashion. Preparative tlc of the crude oil on silica gel (50% ether in hexane) gave (48.8 mg, 52% overall yield) of a foamy product which contained 70% of the β isomer and 30% of the α isomer as judged by vpc (rt 9.8 min. for α isomer, 11.5 min for β isomer, 4' 3% ov 1, 220°). The foamy product was dissolved in ethanol and crystals began to form after a few minutes. After standing at room temperature overnight, the crystals were collected by filtration. Two recrystallizations from hexane gave pure β-isomer: mp 185°–187°; vpc displayed one peak (rt 12.8 min, 4' 3% ov 1, 220°).

The mother liquor from hexane was rotary evaporated and the residue was purified by recrystallization from ethanol to obtain a mixture of 65% α-isomer and 35% β-isomer. (6' 3% ov 17, 245°, rt 29 minutes for α isomer, rt 35 minutes for β-isomer.) The mixture was equilbrated by heating with 10 ml of 2% KOH in methanol-water (4:1) under nitrogen at 70° for 4 hours. The resulting mixture contained 30% α isomer, and 70% β-isomer (by vpc and nmr). The pure β isomer (one peak by vpc) was also subjected to 2% KOH in methanol-water (4:1) at 70° under nitrogen for 4 hours. The resulting mixture contained 30% α isomer and 70% β isomer (by vpc and nmr).

The product of this preparation is reported to have useful pharmacological properties in U.S. Pat. No. 3,254,095.

EXAMPLE 27

17-benzoyl-5β-androstene-1

In a 10 ml round bottom flask equipped with magnetic stirrer and nitrogen inlet was placed 42 mg (0.115 mmole) of the alcohol of Example 11 and 2.5 ml of acetone. The solution was stirred under nitrogen, cooled to 0° and deaerated. The cooling bath was adjusted to 5°–10° and 0.45 ml (0.12 mmole) of Jones reagent was added over 2 minutes. After stirring for an additional 15 minutes, isopropanol was added to destroy excess chromic acid. After diluting with 2 ml water, 2 ml brine and 2 ml ether, the mixture was stirred, the layers separated and the aqueous phase extracted with ethyl acetate. The combined organic layers were washed with 1:1 5% sodium hydroxide-brine solution, followed by a brine washing, filtered and concentrated under reduced pressure to provide the ketonic product.

EXAMPLE 28

1,2-dibromo-5β-17-benzoylandrostane

To approximately 100 mg (0.4 mM) of the crude product of Example 27 in 5 ml chloroform and −10° to −20° is carefully added 0.4 mmole bromine until the color is no longer discharged. All of the volatiles are then removed in vaco and the resulting residue used directly.

EXAMPLE 29

17-hydroxyandrostene-1

In a flask equipped with a stirrer is prepared a slurry of about 58 mg (0.088 mmole) of the ketone of Example 28, 1 ml of dry dichloromethane and 191 mg (1.31 mmole) of oven-dried dibasic sodium phosphate. After cooling the mixture to 0°, 0.5 ml (0.45 mmole peracid) of a solution of peroxytrifluoroacetic acid (prepared by the addition of 0.024 ml of 90% hydrogen peroxide and 0.146 ml of trifluoroacetic anhydride to 1 ml of dichloromethane at 0° followed by stirring for 0.5 hours) is added via syringe with stirring. After the reaction mixture is allowed to warm to room temperature, the flask is sealed and the mixture stirred in the dark for 11 days. On the 4th and 8th days of reaction, additional 0.45 mmole portions of the peracid are added. After 11 days, the reaction is worked up by pouring the mixture onto 5 ml of water overlaid with 5 ml ethyl acetate. The layers are separated and the aqueous phase extracted with ethyl acetate (3×3 ml). The combined organic layers are then worked up in the usual manner to leave the benzoate ester.

The crude benzoate ester is dissolved in approximately 5 ml of diethyl ether and a trace of glacial acetic acid added. To the mixture is then cautiously added approximately 40 mg of zinc dust over a period of about 1 to 2 minutes at ambient temperatures. The mixture is stirred for 20–30 minutes, followed by the addition of water. The layers are separated, the aqueous layer extracted with diethyl ether and the combined organic extracts are washed in sequence with 5% hydrochloric acid, water (3 times), 10% sodium hydroxide, followed by drying over magnesium sulfate.

The ester was then cleaved to provide the alchol by stirring the crude product in 1 ml of dry ether at 0° with 2 spatula tips of lithium aluminum hydride for 45 minutes. Excess hydride is decomposed by cautiously adding 5% sodium hydroxide solution. After filtering and washing the precipitate with ether, the combined organic layers are dried over magnesium sulfate, filtered, and volatiles removed in vacuo. The crude product is then purified by prepative tlc using continuous elution technique for 1.25 hours with 30% ethyl acetate in hexane eluant. The bands are visualized by searing with a hot wire.

The above alcohol can be transformed to known physiological steroids by known techniques. See Morton and Johnson, J. Am. Chem. Soc. 95, 4419 (1973)

The tetracyclic compounds of this invention can be transformed to a number of different known steroids having physiological activity. The cyclization of the subject compounds provide for a $\Delta^1$-A ring or a $\Delta^{3(5)}$3-methyl-A-nor ring of the tetracyclic structure of a steroid. In addition, the cyclization provides for a 17-aroyl substituent.

As for the A ring, that $\Delta^1$-A ring can be transformed by known reactions to the 3-one or 3-ol, the 3-one- 4-ene, the 3-ol-5 ene, or other functionalities as desired. For example, Morton and Johnson, J. Am. Chem. Soc., 95, 4419 (1973) teach the transformation of $\Delta^1$-androsten-17-ol to testosterone benzoate, which can be readily hydrolyzed to testosterone. U.S. Pat. No. 3,156,711 teaches the utility of $\Delta^1$-androsten-17-ol as anabolic-androgenic agents and its transformation to a number of other useful compounds, such as $\Delta^1$-androsten-17-one. (See Examples I & III, Col. 3 of the referenced patent.

Examples 27–30 of the subject application show the transformation of the 17-aroyl to 17-hydroxy.

The transformation of the A-ring from $\Delta^1$- to 3-one-4-ene and 3-one-1, 4-diene is shown in McCarry et al, J. Am. Chem. Soc., 95, 4416 (1973). While the C-17 substituent is acetyl, the same series of transformations would be applicable to an aroyl C-17 substituent. The 3-one-4-ene-17-aroyl compounds are shown to be useful in U.S. Pat. No. 3,254,095.

The A-nor-3(5)-en structure produced by the cyclopentene derivative cyclization has been shown to be transformed to the 3-one-4-ene derivative in Examples 25 and 26. The following synthetic procedure shows the transformation of the A-nor tetracyclic compound to the known 4-androsten-3, 17-dione capable of selective reduction to testosterone (Norymberskiand and Woods, J. Chem. Soc. 1955, 3426; Fajkos, Coll. Czech. Chem. Comm., 24 2284 (1959), Muscher and Fisher, Helv. Chim. Acta, 22, 158 (1939) and Sondheimer et al, J. Am. Chem. Soc., 75, 5930 (1953).

The following provides a flow chart of the compounds and the synthetic procedures.

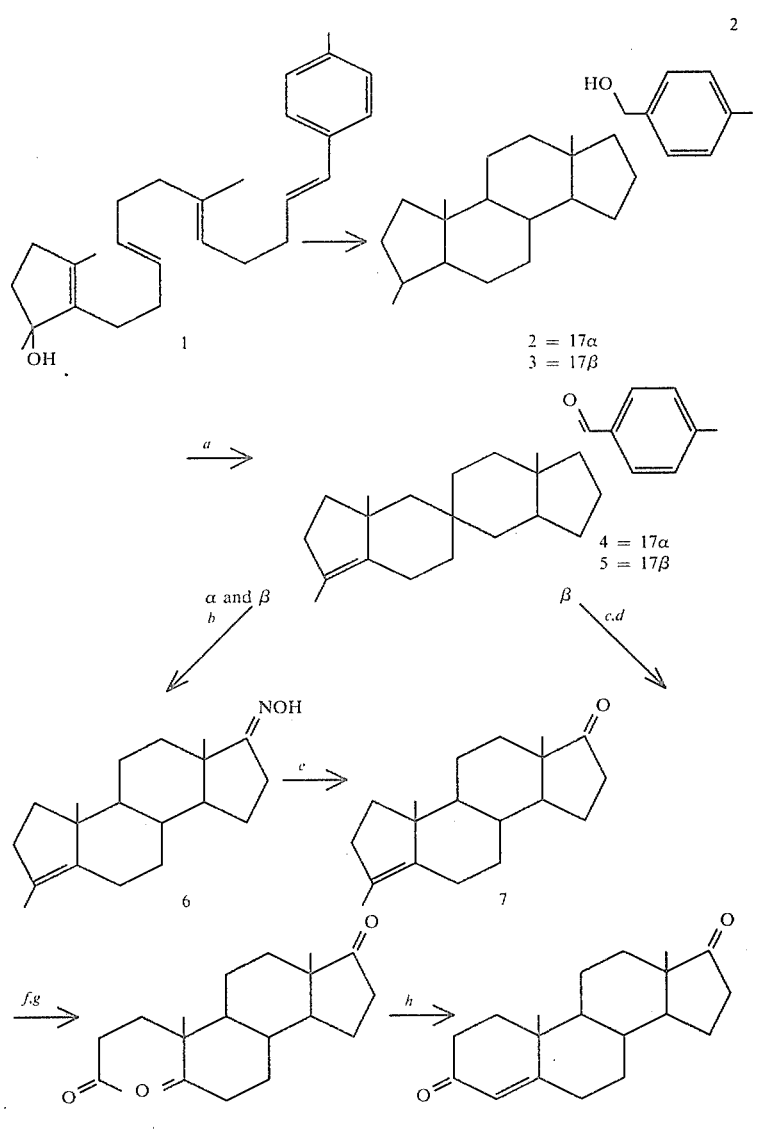

$^a$ MnO$_2$;
$^b$ KOt-Bu;MeONO;
$^c$ KOt-Bu;O$_2$;
$^d$ 80°;
$^e$ HCl,H$_2$CO;
$^f$ O$_3$;
$^g$ Zn—HOAc;
$^h$ KOH.

The following are the synthetic procedures for the preparation of the various compounds and the literature references providing descriptions of the procedures which were adapted to the compounds of the subject invention.

Ex. A.

17α-(p-Methylbenzoyl)-3-methyl-A-nor-3(5)-androstene, (4)

A suspension of 102.0 mg (0.269 mmol) of chromatographed 17α-(α-hydroxy-p-methylbenzyl)-3-methyl-A-nor-3(5)-androstene, 2 (obtained from cyclization of 1), and 510 mg (5.87 mmol, 21.8 eq.) of activated manganese dioxide (Winthrop, dried overnight at 100°) in 25 ml of dry dichloromethane was stirred for 34 h. TLC (20:5:1 hexane:dichloromethane:acetone) of the mixture showed a major new UV-active product ($R_f$=0.57) as well as traces of starting alcohol ($R_f$=0.42) and baseline impurities. Then 5 ml of methanol was added and the mixture stirred for 15 min to displace any product adsorbed onto the oxidant. Celite was added to the mixture, then the slurry was filtered and washed with 200 ml of ether, 200 ml of acetone and 100 ml of methanol. Removal of the solvent from the filtrate at reduced pressure yielded 99.9 mg (98%) of a viscous oil. Chromatography of the crude product on 20 g of Florosil (petroleum ether→3:1. Petroleum ether:dichloromethane) yielded 85.8 mg (84.6%) of the desired ketone 4. A small sample of 4 from a similar oxidation was recrystallized twice from methanol and dried at 56°, 1 mm to afford an analytical sample: mp 149°–153°.

(The procedure was adapted from Pratt and Van de Castle, J. Org. Chem. 26, 2973 (1961)).

Ex. B.

17β-(p-Methylbenzoyl)-3-methyl-A-nor-3(5)-androstene, (5)

A suspension of 148.0 mg (0.391 mmol) of chromatographed 17β-(α-hydroxy-p-methylbenzyl-3-methyl-A-nor-3(5)androstene, 3 (also obtained from cyclization of 1), and 740 mg (8.51 mmol, 21.8 eq.) of activated manganese dioxide (Winthrop, dried overnight at 100°) in 50 ml of dry dichloromethane was stirred at room temperature. After the first 24 h an additional 740 mg (8.51 mmol, 21.8 eq.) of manganese dioxide was added. After a total of 4 days VPC (6' 3% XE-60, 240°) indicated that less than 1% of the starting alcohol (7.0 min.) remained and that only one new product had been formed (8.1 min). Then 10 ml of methanol was added and the reaction mixture stirred for 1 h to displace any product absorbed onto the oxidant. Celite was added to the mixture, then the slurry was filtered and washed with 200 ml of ether, 200 ml of acetone and 100 ml of methanol. The solvent was removed from the filtrate on the rotary evaporator and the resulting oil was filtered through a 1 g plug of Florosil with ether to remove traces of manganese dioxide. Removal of the solvent at reduced pressure yielded 140 mg (95%) of a viscous oil. Chromatography of the crude product on 16 g of Florosil (petroleum ether→5:1 petroleum ether:ether) yielded 99.7 mg (67.7%) of the desired ketone 5. A small sample of 5 from a similar oxidation was recrystallized three times from methanol to afford an analytical sample: mp 156°–158°.

Ex. C

3-Methyl-A-norandrost-3(5)-en-17-one oxime (6)

The procedure was adapted from Woodward and von E. Doering, J. Am. Chem. Soc. 67, 860 (1945) and Harting and Crossley Org. Syn. Coll. Vol. II 363 (1943). A mixture of benzylic alcohols from cyclization of 1 was oxidized as described above to yield 157.0 mg (0.417 mmol) of a 48:52 mixture of 17α- and 17β-phenyl ketones 4 and 5 (97% pure by VPC). A cold (−78°), rigorously deoxygenated solution of 390 mg (3.48 mmol, 8.3 eq.) of potassium t-butoxide (Alfa, t-butanol free) in 39 ml of dry dimethoxyethane was added via syringe to this mixture of ketones at −61° (liquid nitrogen-chloroform bath) in an oven-dried oxygen-free 100 ml three-necked round-bottomed flask equipped with a magnetic stirrer and a nitrogen vacuum inlet. Then approximately 3 ml (50 mmol) of dry, oxygen-free methyl nitrite was distilled into the reaction mixture via a canella. After stirring for 50 minutes, dry carbon dioxide (Matheson) was bubbled in for 30 min. at −61° and then for an additional 30 min. as the reaction mixture warmed to room temperature. The reaction mixture was added to saturated aqueous ammonium chloride and the crude product was isolated as usual by ether extraction. Removal of the solvent by rotary evaporation afforded 180.6 mg (99%) of a slightly yellowish solid. VPC analysis (6' 3% XE-60, 105°–280°) showed in order of increasing retention time: a large amount of methyl p-toluate (confirmed by coinjection of an authentic sample), traces of a similar product (probably either t-butyl p-toluate or p-toluic acid, a small amount of a product believed to have arisen from impurities in the starting material, a large amount of the desired oxime 6, and traces of starting 17α-ketone, 4. TLC (4:2:1 petroleum ether:dichloromethane:acetone) showed two major products: $R_f$ 0.59, UV-active and $R_f$ 0.40, UV-inactive. Chromatography of the crude product on silica gel (dichloromethane→10:1 dichloromethane:ether) yielded 92.4 mg (77.1%) of crystalline oxime 6. A small sample of 6 was recrystallized twice from methanol and dried at 56°, 1 mm to afford an analytical sample: mp 190°–194.5°.

Ex. D

3-Methyl-A-norandrost-3(5)-en-17-one (7)

(a) From Ketone (5)

The method was adapted from Siddall et al, Chem. and Ind. Ind., 1966, 25. A cold (−78° C.), deoxygenated solution of 369 mg (3.30 mmol, 10.4 eq.) of potassium t-butoxide (Alfa, t-butanol free) in 25 ml of dry dimethoxyethane was added to 119.8 mg (0.318 mmol) of pure 17β-phenyl ketone 5 in an oven-dried, oxygen-free 100 ml three-necked round-bottomed flask equipped with a magnetic stirrer and a nitrogen/vacuum inlet at −78°. After stirring 15 min oxygen (99.6%, Liquid Carbonic) was bubbled in slowly. After 20 minutes TLC showed no remaining starting material in solution, but some of the starting ketone appeared to have remained undissolved. An additional 20 ml of cold dry dimethoxyethane was added slowly producing a homogeneous solution. After a total of 1 h. the cold solution was thoroughly deoxygenated under reduced pressure and then heated to boiling. After stirring at approximately 80° for 20 minutes, the reaction mixture was allowed to cool. The reaction was quenched by addition via syringe of 10 ml of saturated, deoxygenated ammonium chloride.

Extraction with ether and work up in the usual manner with a bicarbonate wash (with minor mechanical losses) yielded 89.7 mg (103%) of a yellow oil after removal of solvent at reduced pressure. Chromatography on 25 g of Florosil (petroleum ether→10:1 petroleum ether:ether) afforded 75.3 mg (86.9%) of pure crystalline ketone 7. A small sample of 7 was recrystallized twice from methanol (mp 103°-107°) and then dried with some sublimation at 56°, 1 mm (mp 108.5-109.5).

(b) From Oxime (6)

The procedure was adapted from Cava et al, J. Am. Chem. Soc., 80 2257 (1958). A solution of 55.6 mg (0.200 mmol) of oxime 6, 1.6 ml (100 eq.) of 37% aqueous formaldehyde (MCB reagent), 18 ml of THF, and 2.1 ml of concentrated hydrochloric acid was magnetically stirred in a 50 ml round-bottomed flask at room temperature for 2 h. TLC (4:2:1 hexane:dichloromethane:acetone, $I_2$) showed that starting material of $R_f=0.37$ had been completely replaced by a single new product of $R_f=0.66$. VPC (6' 3% XE-60, 210°) showed that the starting oxime (4.6 min.) was gone and that a major product (2.7 min) as well as several minor products (shorter retention times) had been formed. The reaction mixture was quenched with aqueous sodium bicarbonate and extracted with dichloromethane. Work-up in the usual manner and removal of solvent at reduced pressure yielded 361.6 mg of the desired ketone and formaldehyde polymers. Chromatography on 17 g of Florosil (petroleum ether→10:1—petroleum ether:ether) yielded 77.4 mg (147%) of yellow oil. Sublimation (80°, 0.5 mm, 24 hours) of this oil afforded 66.4 mg (126%) of white solid. Rechromatography on 11 g of silica gel (petroleum ether→20:1—petroleum ether:ether) yielded 34.4 mg (65.3%) of the desired ketone 7 (94% pure by VPC: 6' 3% XE 60, 150°-250°) which was identical in all respects to the oxygenation product described previously.

Ex. E

Seco-4,5-androstane-3,5,17-trione (8)

The procedure was adapted from Johnson, et al, J. Am. Chem. Soc., 93, 4332 (1971) Ozone (Welsbach ozonizer, 0.1 mmol/min) was bubbled into an ozonolysis tube containing a −78° solution of 52.5 mg (0.193 mmol, pure by VPC) of ketone 7 in 5 ml of methanol and 5 ml of dichloromethane until a deep blue color developed (2 min). The excess ozone was removed by bubbling in nitrogen as the reaction mixture warmed to room temperature. Then 220 mg (3.36 mmol, 17 eq) of zinc dust (Mallinkrodt reagent) and 3 ml of glacial acetic acid (Baker reagent) were added and the resulting suspension was stirred vigorously for 4.5 hours. The reaction was quenched slowly with excess aqueous sodium bicarbonate and stirred until carbon dioxide evolution ceased. Extraction with dichloromethane and work up in the usual manner afforded 59.1 mg (101%) of colorless oil after removing solvent at reduced pressure. VPC (6' 3% XE-60, 246°) showed one major peak for the desired triketone (5.8 min) along with small amounts of androst-4-ene-3,17-dione from acid-catalyzed aldol condensation (8.0 min) and an unknown impurity (3.3 min). The crude product was used in the following reaction without further purification.

Ex. F

Androst-4-ene-3,17-dione (9)

The procedure was adapted from Johnson, et al, J. Am. Chem. Soc., 93, 4332 (1971). A solution of the crude triketone described above (59.1 mg crude, actually only 0.193 mmol) in 8 ml of methanol, 2 ml of 5% aqueous hydroxide and 10 ml of tetrahydrofuran in a 50 ml round-bottomed flask equipped with a magnetic stirrer and a nitrogen/vacuum inlet was deoxygenated and stirred overnight (12 h) at room temperature. VPC and TLC showed that no triketone remained. The reaction mixture was poured into aqueous ammonium chloride and extracted with dichloromethane. Work up in the usual manner followed by removal of solvent at reduced pressure yielded 55.5 mg (101%) of yellow oil. Chromatography on 20 g of Activity IV basic alumina (ether) afforded 38 mg (68.8%) of crystalline white solid (<99% pure by VPC). This material was identical in all respects (IR, NMR, TLC, GC) with authentic d-androst-4-ene-3,7-dione which had been prepared by oxidation of d-testosterone.

In addition to the above examples and references, applicable transformations of the compounds of the subject invention or products obtained from them may be found in the following prior art references.

Johnson, Chimia 29, 310 (1975) describes the transformation of the A ring from the A-nor-3(5)-3-methylprogesterone having a C-11 hydroxyl substituent. See also, Johnson, et al J. Am. Chem. Soc. 98, 1039 (1976) and references cited therein. Johnson and Dubois, J. Am. Chem. Soc., 98, 1038 (1976) describe transformation of the A ring from the A-nor-3(5)-3-methyl-progesterone having a C-11 methyl substituent.

The following examples are offered to illustrate cyclization to lower polycyclics, such as bicyclics. In addition, a different initiator was used than was employed in the cyclization of the steroid products.

EXAMPLE 30 trans-1-methylcyclopropyl 1-carbomethoxy-4-phenyl-3-butenyl ketone

To an oven-dried, 250 ml 3-necked flask equipped with magnetic stirrer, dropping funnel, and nitrogen inlet was added 2.79 g of sodium hydride (57% of an oil dispersion; 1.59 g, 0.0663 g-atom), the sodium hydride was washed with dry pentane (3×75 ml), the pentane removed and 60 ml of dry tetrahydrofuran added. The gray suspension was cooled in an ice-water bath. A solution of 9.38 g (0.060 mole) of 1-methylcyclopropyl carbomethoxymethyl ketone in 60 ml of dry tetrahydrofuran was then added dropwise over a period of 30 minutes to the hydride suspension. The cooling bath was removed, the yellow solution stirred for 2 hours at room temperature and then filtered through a Celite pad. The filtrate was concentrated under reduced pressure to afford a pale yellow solid which was used directly for alkylation.

To an oven-dried, 100 ml 3-necked flask equipped with a magnetic stirrer, dropping funnel, reflux condenser, and nitrogen inlet, was charged 8.25 g (0.055 mole) of sodium iodide and 10 ml of acetonitrile, followed by a solution of 7.63 g (0.050 mole) of trans-(3-chloropropenyl)benzene in 10 ml of dry tetrahydrofuran added by syringe. The resulting mixture was stirred at 0°-5° for 45 minutes after which time the cooling bath was removed. A solution of the above sodium enolate in 20 ml of acetonitrile and 10 ml of dimethylformamide was then added over a period of 25 minutes. After addition was complete, the reaction mixture was stirred for 3 hours at room temperature and than at 60°-70° for 18 hours. After cooling to room temperature, the yellow reaction mixture was poured into 100 ml of 50:50 5% hydrochloric acid/brine. The mixture was extracted with ether (3×50 ml), and the combined extracts were washed with saturated sodium bicarbonate (3×50 ml) then dried over magnesium sulfate. Rotary evaporation of solvent afforded 13.1 g of a yellow liquid.

The crude keto ester product was distilled through a short-path apparatus to afford 11.14 g of a pale yellow liquid, bp 131°–142°/0.008 mm (82% yield, 94% pure by vpc).

EXAMPLE 31 trans-1-methylcyclopropyl 4-phenyl-3-butenyl ketone

To a one liter round-bottom flask equipped with magnetic stirrer, reflux condenser, and nitrogen inlet was charged 87.5 g (0.277 mole) of barium hydroxide octahydrate, 300 ml of water, followed by a solution of 12.9 g (0.0474 mole) of distilled keto ester (Ex. 30) in 90 ml of 95% ethanol. The resultant mixture was stirred and deaerated followed by refluxing for 22 hours under nitrogen. The reaction mixture was then cooled to room temperature, dissolved in 180 ml of benzene, and brought to a pH of 1 with 10% hydrochloric acid. The total volume was brought to 900 ml with brine and the phases separated. The aqueous phase was extracted with benzene (2×180 ml), the combined organic layers washed with 5% sodium hydroxide solution (2×120 ml), $H_2O$ (2×120 ml), and brine (2×120 ml) and dried over sodium sulfate, followed by rotary evaporation of solvent to afford 9.9 g of a yellow liquid.

Distillation of the crude product on a short-path apparatus yielded 9.50 g of the ketone product as a colorless liquid, bp 123°–126°/0.025 mm (94% yield, >99% pure by vpc).

EXAMPLE 32 trans-1-methylcyclopropyl-4-phenyl-3-butenylcarbinol

Lithium aluminum hydride (2.33 g, 0.0614 mole) and 225 ml of anhydrous ether were placed in a flame-dried, 500 ml 3-necked flask fitted with magnetic stirrer, dropping funnel, and reflux condenser equipped with a nitrogen inlet. The suspension was cooled to 0° with an ice-water bath, and a solution of 9.31 g (0.0434 mole) of cyclopropyl ketone (Ex. 31) in 125 ml of anhydrous ether was carefully added through the dropping funnel. The mixture was stirred at 0° under a nitrogen atmosphere for 2 hours before the excess hydride was decomposed by the cautious addition of a 5% solution of sodium hydroxide. The white precipitate was filtered and washed with several portions of ether. The ethereal solution was then dried over sodium sulfate and concentrated under reduced pressure to give 9.35 g of a colorless liquid (99% yield).

EXAMPLE 33 trans,trans-1-bromo-3-methyl-8-phenyl-3,7-octadiene

To a dry, one liter 3-necked flask fitted with magnetic stirrer, reflux condenser, and dropping funnel with nitrogen inlet were added 8.88 g (0.0410 mole) of cyclopropyl carbinol (Ex. 32) in 200 ml of dry ether, 3.82 g (0.0442 mole) of anhydrous lithium bromide, and 19.4 g (0.160 mole) of s-collidine. The resultant suspension was then cooled to −78° under an atmosphere of nitrogen. To the rapidly stirred mixture was added dropwise a solution of 4.06 ml (11.58 g, 0.0428 mole) of phosphorus tribromide in 150 ml of dry ether over a period of 65 minutes causing a voluminous amount of a white precipitate to form. The reaction mixture was then allowed to warm to room temperature and was stirred for 20 hours. After this period of time, 10 ml of collidine was added to the reaction mixture and the flask was cooled to 0°. This was followed by the careful addition of 32 ml of water, and the resultant clear solution was poured into 250 ml of 50% brine overlaid with 125 ml of pentane. The aqueous phase was extracted with pentane (3×125 ml) and the combined organic layers were washed with water (125 ml) and ice-cold 5% hydrochloric acid (4×125 ml) followed by the usual workup. Drying over anhydrous potassium carbonate and rotary evaporation of solvent afforded 10.1 g of a pale yellow liquid. This material was not characterized but was used directly in the rearrangement reaction described below.

In a 500 ml 3-necked flask was placed 49.0 g (0.217 mole) of zinc bromide and a magnetic stirring bar. The zinc bromide was then flame dried under vacuum until it reached a fine, sand-like consistency. (Care must be exercised to prevent fusion of the salt.) The flask was equipped with a dropping funnel and nitrogen inlet and 200 ml of dry ether was then added. The dropping funnel was charged with a solution of 10.1 g of the crude bromide described above in 120 ml of dry ether which after cooling the reaction vessel to 0°, was added dropwise over a period of 60 minutes to the reaction flask. The resultant mixture was stirred at 0° for an additional 4 hours before it was poured onto 225 ml of 50% brine overlaid with 225 ml of pentane. The aqueous phase was extracted with pentane (3×150 ml), and the combined organic portions washed with water (300 ml) and brine (300 ml), dried over potassium carbonate, and concentrated under reduced pressure to give 9.17 g (80% yield from alcohol) of a cloudy-yellow liquid.

EXAMPLE 34 lithium 3-methyl-2-butenoate

In a dry, 500 ml 3-necked flask equipped with dropping funnel, mechanical stirrer, reflux condenser, and nitrogen inlet were placed 0.80 g (0.100 mole) of lithium hydride (finely pulverized) and 20 ml of dry ether. The dropping funnel was charged with a solution of 10.2 g (0.102 mole) of 3-methyl-2-butenoic acid dissolved in 300 ml of dry ether. The suspension of hydride was stirred mechanically under nitrogen while the ethereal solution of acid was added over a 20 minute period. The reaction mixture was stirred at room temperature for 22 hours after which time period the white precipitate was filtered and washed with portions of ether. The solid was then dried in a vacuum desiccator to afford 9.96 g (93% yield) of a white powder.

EXAMPLE 35 trans,trans-3-carbomethoxy-2,6-dimethyl-11-phenyl-1,6,10-undecatriene

A dry, 250 ml 3-necked flask was equipped with a magnetic stirrer and nitrogen inlet and was charged with 12.56 g (0.124 mole) of N,N-diisopropylamine and 31 ml of dry tetrahydrofuran. The solution was cooled to 0° under an atmosphere of nitrogen and 49.0 ml (2.53 M, 0.124 mole) of a hexane solution of n-butyllithium was added via syringe. The solution was stirred 5 minutes and was then added via syringe to a slurry of 13.15 g (0.124 mole) of lithium 3-methyl-2-butenoate in 93 ml of dry tetrahydrofuran, which had been pre-cooled to 0°, over a period of 10 minutes. The yellow suspension of dianion was stirred at 0° for 30 minutes and then cooled to −78°. To this suspension was added via syringe over a period of 10 minutes a solution of 8.65 g (0.0310 mole) of the homoallylic bromide (Ex. 33) in 62 ml of dry tetrahydrofuran. After the addition of bromide was complete, the dry ice-acetone bath was replaced with an ice-water bath and stirring under nitrogen was continued for 25 hours while the reaction mixture slowly warmed to room temperature as the ice melted in the cooling bath.

The yellow mixture was then poured into 500 ml of a 5% solution of sodium hydroxide and the resulting mixture extracted with 1:1 ether-hexane (3×250 ml). The organic layers were combined and extracted back with water (2×100 ml). The combined aqueous portions were then cooled in an ice-water bath and acidified with 10% hydrochloric acid to a pH of 1. The white, aqueous phase was then extracted with benzene (2×500 ml) and ether (2×250 ml). The combined organic layers were then washed with water (2×250 ml) and brine (500 ml), dried over sodium sulfate, and evaporated at reduced pressure to afford 13.63 g of a bright yellow liquid. The crude acid thus obtained was approximately 50% by weight of the alkylated triene acid product and 50% unreacted 3-methyl-2-butenoic acid.

To a 500 ml round-bottom flask was added 13.33 g (ca. 0.10 mole of carboxylic acid) of crude acid prepared above, 200 ml of anhydrous acetone, 27.7 g (0.20 mole) of potassium carbonate, and 28.4 g (0.20 mole) of methyl iodide. The flask was equipped with a magnetic stirrer, reflux condenser, and nitrogen inlet. The mixture was cooled to −70° and deaerated, followed by stirring and refluxing for 1¾ hours. The yellow suspension was cooled to room temperature and poured into 220 ml of water. The mixture was extracted with ether (3×180 ml), and the combined organic portions were washed with a 10% solution of sodium thiosulfate (1×180 ml), brine (1×180 ml), filtered, and then dried over magnesium sulfate. Removal of solvent under reduced pressure yielded 13.18 g of a yellow liquid.

The crude ester was applied to a 300 g column of silica gel (60–200 mesh) and eluted with 1–3% solutions of ether in hexane. A total of 6.82 g (0.0219 mole, 70% yield based on homoallylic bromide) of the ester was collected.

EXAMPLE 36 trans,trans-3-carbomethoxy-2,6-dimethyl-11-phenyl-2,6,10-undecatriene

To a dry, 250 ml round-bottom flask fitted with magnetic stirrer and serum cap was added 6.73 g (0.0215 mole) of β,γ-unsaturated ester (Ex. 35) and 60 ml of dry t-butyl alcohol (refluxed 24 hours over sodium and distilled from the active metal). The solution was dearated and 30.2 ml of a 5% by weight solution of potassium t-butoxide in dry t-butyl alcohol (0.0108 mole, 0.5 equivalent base) was added via syringe. The solution turned a bright yellow color and was stirred under nitrogen at room temperature for 5¾ hours. The reaction mixture was then poured into 275 ml of a 50:50 solution of 10% hydrochloric acid and brine overlaid with 250 ml of pentane. The layers were separated and the aqueous phase extracted with pentane (2×150 ml). The combined organic layers were washed with water (250 ml) and brine (250 ml) and worked up in the usual manner to afford 6.70 g of a yellow liquid. The crude product was distilled bulb-to-bulb at 150°/0.015 mm, yielding 6.46 g (96% yield) of a pale yellow liquid.

EXAMPLE 37 trans,trans-2-hydroxy-3-isopropylidene-2,6-dimethyl-11-phenyl-6,10-undecadiene

In a dry, 50 ml 3-necked flask equipped with magnetic stirrer, reflux condenser, serum cap and nitrogen inlet was placed 0.317 g (1.01 mmole) of the above described ester and 23 ml of dry ether. The solution was stirred under nitrogen at room temperature as 2.0 ml (2.26 M, 0.00452 mole) of a methyllithium in hexane solution was added via syringe. Stirring was continued for 20 minutes before excess methyllithium was quenched by the careful addition of methanol. The contents of the flask were poured into 20 ml of water and the phases separated. The aqueous layer was extracted with ether (2×20 ml), the combined organic layers washed with water and worked up as usual to afford 0.310 g (98% yield) of a pale yellow liquid. This product could be chromatographed on a column of 20% silver nitrate impregnated neutral alumina eluting with ethyl acetate/hexane mixtures (40% or greater ethyl acetate solutions eluted the desired alcohol) to improve the product purity to >90% of the desired alcohol.

EXAMPLE 38 cyclization to 1α-(α-hydroxybenzyl)-4,4,9β-trimethyl-5-isopropylidene-8α-hydrindane In a dry 100 ml round-bottom flask equipped with nitrogen inlet and magnetic stirrer was placed 0.242 g (90% pure by vpc; 0.695 mmole, nominal) of tertiary alcohol (Ex. 37) prepared as described above (contaminated with the β,γ-isomer) and 35 ml of dry, purified dichloromethane. The solution was cooled to −78° and thoroughly deaerated with nitrogen. To the rapidly stirred solution was added via syringe 2.65 ml of a solution containing 0.350 g trifluoroacetic acid in 3.0 ml of dichloromethane solution (0.309 TFA, 0.00271 mole, 3.9 equivalents) over 3 minutes. The resultant yellow-orange reaction mixture was stirred an additional 8 minutes and then was quenched by pouring onto 40 ml of saturated sodium bicarbonate solution overlaid with 40 ml of ether. The layers were separated and the aqueous phase extracted with ether (2×40 ml). The combined organic layers were worked up as usual to afford 0.300 g of a pale yellow liquid.

Without further purification, the crude ester was placed in a 50 ml flask and dissolved in 24 ml of methanol. Water (9.6 ml) was added and the milky mixture was deaerated with nitrogen before 0.810 g of potassium carbonate was added. The resultant mixture was then stirred magnetically under nitrogen at room temperature for 18 hours. After this time, the reaction mixture was concentrated on the rotary evaporator to remove most of the methanol. The remaining mixture was extracted with ethyl acetate (6×10 ml) and the combined organic extracts worked up in the usual manner to afford 0.246 g of a pale yellow liquid.

Besides the examples which have been previously described, numerous variations are possible which allow for alkyl substituents at various positions of the steroid nucleus, employment of a different initiator, or the like.

For example, if the ethylene glycol acetal of 6-oxo, 2-(H or CH₃)-1-hexenyl-1 is to be employed as the initiator, the methods described in J. Am. Chem. Soc., 95, 2656 (1973) and ibid, 90, 5279 (1970) may be respectively employed. For the 5,6-epoxy-1-hexenyl-1, the method of ibid, 94, 8225, 8228 and 8229 (1972) may be employed. Where an ethylene dithioketal of 2-hydroxy, 3-oxo, 6-methyl-Δ⁶⁽¹⁾-cyclohexenyl-1 initiator is employed, one can employ the methyl cyclohexan-2-on-1-yl, which can be condensed with a formate ester and the double bond cleaved and condensed with ethylene dimercaptan in accordance with the procedures set forth in J. Chem. Soc., 1957, 1131 and J. Org. Chem., 36, 1137 (1971). The ketone may then be reduced to the alcohol in known ways.

Instead of using trialkylorthoacetate in the reaction of the allyl alcohol with the ortho ester, trialkylorthopropionate may be employed introducing a methyl substituent at the 11-position. If 2-bromopropene is replaced with 2-bromobutene in the Grignard condensation with the aldehyde, a C-18 ethyl group will be provided, rather than a methyl group.

Variations in the synthetic procedure may be employed in order to introduce alkyl substituents at various ring positions, which otherwise can only be difficulty introduced from naturally occurring steroids. Thus, the subject method provides substantial versatility in the synthesis of a wide variety of compounds having the steroid nucleus.

The subject method provides a unique terminating group in that good yields are obtained during cyclization of polyunsaturated compounds, whereby an aliphatically unsaturated center interacts with an aromatic ring with resulting stabilization of a carbocation. In the process of cyclization, a carbocation is formed at a remote position from the terminator group and depending upon the number of rings to be formed, will interact with one or more double bonds forming new sigma bonds until the carbocation is captured by the aliphatically unsaturated center in the alpha position to the aromatic ring. The terminator plays a crucial role in the formation of the final product. The nature of the terminator can affect the degree to which cyclization is complete rather than aborted at a lower number of rings. In addition, particularly where alkyl groups are present at nearby carbon atoms, e.g. C-13, the terminating group may affect the degree of rearrangement or migration of various atoms. Finally, the terminating group can affect the nature of the final product and the degree to which the nucleophile reacts at the carbocation center or elimination occurs. In view of the manifold role the terminating group plays the terminating group is sensitive to variations in structure, substitution and the like. In the subject invention, it was found that by having an aromatic group interacting with a positive charge on an alpha carbon atom, cyclization yields were enhanced, cyclization was simplified, and a readily purifiable product was obtained. In addition, the nature of the alpha-hydroxy alkyl substituent at C-17 allows for transformation and degradation to introduce a carbonyl group at C-17, so as to assume the androstane structure.

In addition, the steroidal compounds prepared according to this invention can be used by themselves or in combination with cholesteric liquid crystal compositions to provide compositions having cholesteric liquid crystal properties with varying temperature responses. Usually only about 0.1 to 5 weight percent of the subject compounds will be used to modify the properties of the cholesteric liquid crystal compositions.

Although the foregoing invention has been described in some detail by way of illustration and example for purposes of clarity of understanding, it will be obvious that certain changes and modifications may be practiced within the scope of the appended claims.

What is claimed is:

1. A compound of the formula

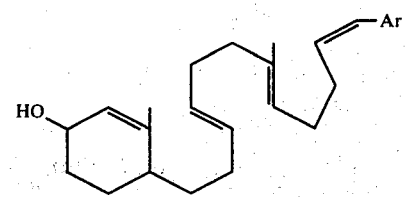

wherein: Ar is phenyl, naphthyl or substituted phenyl, wherein said substituent is alkyl of from 1 to 4 carbon atoms, hydroxy, thiol, alkoxy of up to 4 carbon atoms, or alkylthio of up to 4 carbon atoms.

2. A compound of the formula

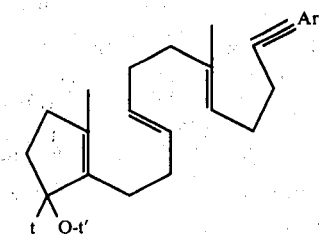

wherein:

Ar is phenyl, substituted phenyl, wherein the substituent is alkyl of from 1 to 4 carbon atoms, hydroxy, thiol, alkoxy or alkylthio of up to 4 carbon atoms, or naphthyl; and t and t' may be taken together to form a bond or t is methyl and t' is hydrogen.

3. A compound which is a member of the group consisting of:

(1) a compound of the formula:

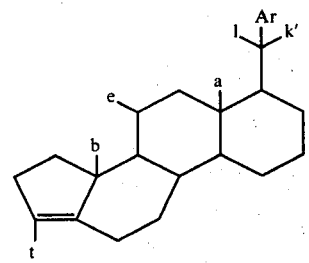

or (2) a compound of the formula:

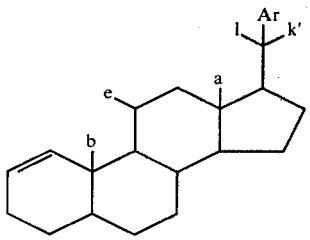

wherein:
a is hydrogen or methyl;
b is hydrogen or methyl;
e is hydrogen, methyl, hydroxy or alkoxy of up to 6 carbon atoms;
Ar is a carbocyclic aromatic compound of from 6 to 12 annular carbon atoms having from 0 to 2 substituents, said substituents selected from the group consisting of hydroxy, thiol, alkoxy of up to 4 carbon atoms, alkylthio of up to 4 carbon atoms, and alkyl of from 1 to 4 carbon atoms;
l is hydroxy and k' is hydrogen, with the proviso that l and k' may be taken together to define oxo; and
t is hydrogen or alkyl of from 1 to 2 carbon atoms.

4. A compound according to claim 3, which is of formula (1), where t is methyl and e is hydrogen.

5. A compound according to claim 4, wherein a and b are methyl.

6. A compound according to claim 3, which is of formula (2) and e is hydrogen.

7. A compound according to claim 6, wherein a and b are methyl.

8. A precursor to a compound according to claim 3, which is a member of the group consisting of:
(1) a compound of the formula:

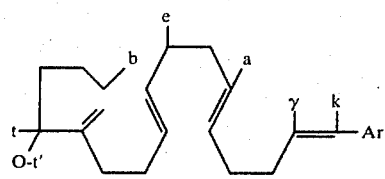

or
(2) a compound of the formula:

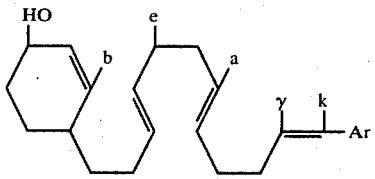

wherein:
a and b are hydrogen or methyl;
e is hydrogen, methyl, hydroxy, or alkoxy of up to 6 carbon atoms;
Ar is a carbocyclic aromatic compound of from 6 to 12 annular carbon atoms having from 0 to 2 substituents, said substituents selected from the group consisting of hydroxy, thiol, alkoxy of up to 4 carbon atoms, alkylthio of up to 4 carbon atoms, and alkyl of from 1 to 4 carbon atoms;
j and k are hydrogen or are taken together to form a bond; and
t and t' are the same as defined in claim 2.

* * * * *